(12) United States Patent
Thiers et al.

(10) Patent No.: US 11,961,596 B2
(45) Date of Patent: *Apr. 16, 2024

(54) SYSTEMS AND METHODS FOR STREAMING NORMALIZED CLINICAL TRIAL CAPACITY INFORMATION

(71) Applicant: IQVIA Inc., Parsippany, NJ (US)

(72) Inventors: Fabio Albuquerque Thiers, New York, NY (US); Henrique Martins da Silva, Sao Paulo (BR)

(73) Assignee: IQVIA Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/841,004

(22) Filed: Jun. 15, 2022

(65) Prior Publication Data

US 2022/0310224 A1    Sep. 29, 2022

Related U.S. Application Data

(63) Continuation of application No. 14/815,425, filed on Jul. 31, 2015, now Pat. No. 11,392,670, which is a continuation-in-part of application No. 13/708,154, filed on Dec. 7, 2012, now abandoned.

(60) Provisional application No. 62/031,492, filed on Jul. 31, 2014, provisional application No. 61/695,797, filed on Aug. 31, 2012, provisional application No. 61/569,098, filed on Dec. 9, 2011.

(51) Int. Cl.
*G16H 10/20* (2018.01)
*G16H 70/40* (2018.01)

(52) U.S. Cl.
CPC ............. *G16H 10/20* (2018.01); *G16H 70/40* (2018.01)

(58) Field of Classification Search
CPC .................................. G16H 10/00–40
USPC ....................................... 705/2, 3
See application file for complete search history.

(56) References Cited

U.S. PATENT DOCUMENTS 6,092,072 A * 7/2000 Guha ................ G06F 18/232
707/700
8,559,926 B1 * 10/2013 Zang ................. H04W 12/126
455/410

(Continued)

FOREIGN PATENT DOCUMENTS

EP       2610776 A2 *  7/2013  ............ G06F 21/56

OTHER PUBLICATIONS

"Note for Guidance on Choice of Control Group in Clinical Trials," European Medicines Agency, Jan. 2001 (Year: 2001).*

(Continued)

*Primary Examiner* — Jonathon A. Szumny
(74) *Attorney, Agent, or Firm* — John Maldjian, Esq.; David L. D'Amato, Esq.; Stevens & Lee PC

(57) ABSTRACT

The invention generally relates to computer-based systems to evaluate and market clinical trial research centers. In certain aspects, the invention provides computer-based systems to collect information about clinical research centers. Systems include a tangible, non-transitory memory coupled to a processor operable to retrieve, based on a user's input, an identity of a clinical research center and prompt the user for information relating generally to the center. The system can collect disease-specific information by prompting the user for a selection of a disease and then collecting from the user information identifying an ability of the center to perform one or more tests relating to the disease.

20 Claims, 30 Drawing Sheets

(56) References Cited

U.S. PATENT DOCUMENTS

| | | | |
|---|---|---|---|
| 8,706,537 | B1 | 4/2014 | Young et al. |
| 2004/0113942 | A1* | 6/2004 | Tomlyn .............. G06F 16/2423 |
| | | | 715/744 |
| 2005/0060305 | A1 | 3/2005 | Hopkins et al. |
| 2005/0102162 | A1 | 5/2005 | Blumenfeld |
| 2005/0119534 | A1 | 6/2005 | Torst et al. |
| 2006/0229916 | A1 | 10/2006 | Michelson et al. |
| 2008/0133270 | A1 | 6/2008 | Michelson et al. |
| 2009/0100363 | A1 | 4/2009 | Pegg et al. |
| 2010/0088245 | A1 | 4/2010 | Harrison et al. |
| 2010/0211411 | A1* | 8/2010 | Hudson ................ G06Q 30/018 |
| | | | 705/317 |
| 2011/0077973 | A1* | 3/2011 | Breitenstein ......... G06F 3/0484 |
| | | | 705/3 |
| 2011/0301967 | A1 | 12/2011 | Friedlander et al. |
| 2012/0269491 | A1* | 10/2012 | Sugano ................. H04N 21/47 |
| | | | 386/230 |
| 2013/0096991 | A1* | 4/2013 | Gardner ............ G06Q 30/0623 |
| | | | 705/7.42 |
| 2013/0114894 | A1* | 5/2013 | Yadav ...................... G06T 5/50 |
| | | | 382/167 |
| 2013/0346381 | A1 | 12/2013 | Ottolenghi |
| 2016/0103964 | A1 | 4/2016 | Osorio et al. |
| 2017/0324805 | A1* | 11/2017 | Charaniya .............. G06F 16/29 |

OTHER PUBLICATIONS

Hernandez, M. (2009), "Visualization for seeking and comparing clinical trials" University of Victoria, Canada (Order No. NR66834) (187 pages total).

\* cited by examiner

| | | | | |
|---|---|---|---|---|
| No. of Publications | 0-10 | 11-20 | 21-40 | 41-150 | 151-200 | 200-300 |
| FDA Filings | 0-10 | 11-20 | 21-40 | 41-150 | 151-200 | 200-300 |
| FDA Inspections | 0-10 | 11-20 | 21-40 | 41-150 | 151-200 | 200-300 |
| No of Trials | 0-10 | 11-20 | 21-40 | 41-150 | 151-200 | 200-300 |
| No. of Trials as PI | 0-10 | 11-20 | 21-40 | 41-150 | 151-200 | 200-300 |

Trial Experience [Phase 1 ▼]

[Next]

FIG. 4

| ViS | Location | Center | Investigator | | 🔍 Search | About ׀ Account ׀ Help ׀ ✉ Contact |

⇐ ⇒ ▴ Arrhythmia | Find Investigator by name | Advanced Investigator Analytics

Home > Investigator > Advanced Investigator Analytics

| Step 1. > Investigator Criteria | Step 2. > Location Criteria | Step 3. > Center Criteria |

Country [United States ⇕] State [Texas ⇕] City [Select ⇕] Add More Location▼

[AND]

| Select Metric ⇕ | 0-10 | 11-20 | 21-40 | 41-150 | 151-200 | 200-300 |

Enrolled Patients
Available Patients
Available Patients by Trails at Site Level
Available Patients by Centers
Engagement Level
Available Patients and Engagement
Trial at Site Level (All)
Trial at Site Level (Phase I)
Trial at Site Level (Phase II)
Trial at Site Level (Phase III)
Trial at Site Level (Phase IV)
Trial at Site Level (Ongoing)
Trial at Site Level & Growth Rate
Centers
Centers and Disease Studied
Centers and Trail per Center
Preference Level
Investigators Select Range

VIS | Location | Center | Investigator | | Q Search | | About | Account | Help | ✉Contact ▼Arrhythmia | Find Investigator by name | | Advanced Investigator Analytics Home > Investigator > Advanced Investigator Analytics Step 1. > Investigator Criteria | Step 2. > Location Criteria | Step 3. > Center Criteria Select Questions > Step 3.1 > About > Step 3.2 > Infrastructure > Step 3.3 > Patients >

1. Are there any other National regulatory approvals (in addition to the one from IRB/IEC) that you must obtain before enrollment can begin at your location?  Yes ○  No ○  In some cases ○

2. Are there any other Local regulatory approvals (in addition to the one from IRB/IEC) that you must obtain before enrollment can begin at your location?  Yes ○  No ○  In some cases ○

3. Is the Local IRB/IEC at your location able to waive authority and use a Central IRB/IEC?  Yes ○  No ○  In some cases ○

4. What is the average number of weeks required from complete submission until ethics approval (local and/or central IRB/IEC), at your location? _____

5. What is the average number of weeks required from complete submission until regulatory approval, at your location? _____

6. How do ethics submission and regulatory submission processes take place at your location?  Parallel ○  Sequential ○

[Next]

| ⇐ ⇒ ↻ | Q | ≡ |

VIS [Location] [Center] [Investigator]　　[Q Search]　About|Account|Help|Contact

▲Arrhythmia　[Find location by city, state, or country]　[Custom Analytics ▼]　[Advanced Center Analytics]

Home > Center > Advanced Center Analytics

| Step 1. > Investigator Criteria | Step 2. > Location Criteria | Step 3. > Center Criteria |

Select Questions > Step 3.1 > About >　Step 3.2 > Infrastructure > Step 3.3 > Patients >

1. Does your center have the capability for evaluating patients with Arrhythmia with the following tests/procedures?

| 1.1 Electrophysiology Study | Yes ○ | No ○ | Can be arranged ○ |

2. Does your center have the capability for evaluating patients with Arrhythmia with the following monitoring devices?

| 2.1 In Hospital Telemetry | Yes ○ | No ○ | Can be arranged ○ |
| 2.2 Holter monitoring | Yes ○ | No ○ | Can be arranged ○ |
| 2.3 External loop recorders | Yes ○ | No ○ | Can be arranged ○ |
| 2.4 Postevent recorders | Yes ○ | No ○ | Can be arranged ○ |
| 2.5 Autodetect recorders | Yes ○ | No ○ | Can be arranged ○ |
| 2.6 Implantable loop recorders | Yes ○ | No ○ | Can be arranged ○ |
| 2.7 Real Time Continuous Cardiac Monitoring system | Yes ○ | No ○ | Can be arranged ○ |

[Next]

FIG. 8

| ⇐ ⇒ ⟳ | 🔍 | | | ≡ |

VIS | Location | Center | Investigator | 🔍 Search | About | Account | Help | ✉ Contact
▲ Arrhythmia | Find investigator by name | Advanced Center Analytics Home > Center > Advanced Center Analytics
Step 1. > Investigator Criteria | Step 2. > Location Criteria | Step 3. > Center Criteria
Select Questions > Step 3.1 > About > Step 3.2 > Infrastructure > Step 3.3 > Patients >

| Question | Options | |
|---|---|---|
| 1. What is the number of Arrhythmia patients in your center database as of July 21, 2014? | | |
| 2. What is the number of new Arrhythmia patients that enter your center database every month? | | |
| 3. What is the gender distribution (%) of patients with Arrhythmia in your center database?(should add up to 100%) | Female | Answer |
| | Male | Answer |
| 4. What is the age distribution (%) of patients with Arrhythmia in your center database? (should add up to 100%) | Under one year | Answer |
| | 1-14 years | Answer |
| | 15-44 years | Answer |
| | 45-64 years | Answer |
| | 65+ years | Answer |
| 5. what is the proportion (%) of patients with Arrhythmia having the following types as per origin, you see at your center per month?(should add up to 100%) | Atrial | Answer |
| | Ventricular | Answer |
| | junctional | Answer |
| | Atrio-Ventricular | Answer |
| | Unknown | Answer |

Search Investigators

```
⇐ ⇒ ↻ [🔍                                                              ] ≡
  VIS |Location|Center|Investigator|      [🔍Search        ] About|Account|Help|✉Contact
  ▴Arrhythmia    [Find location by city, state, or country] [Custom Anaytics ▾] [Advanced Center Analytics]
  Home > Center > Advanced Center Analytics
              [Step 1. > Investigator Criteria|Step 2. > Location Criteria|Step 3. > Center Criteria]
          Country  [United States ◆] State [Texas ◆] City [Select ◆]  Add More Location ▾
                                  [AND]

Select Metric ◆  [0-10 | 11-20 | 21-40 | 41-150 | 151-200 | 200-300]
          Enrolled Patients                    Select Range
          Available Patients
          Available Patients by Trials at Site Level
          Available Patients by Centers
          Engagement Level
          Available Patients and Engagement
          Trial at Site Level (All)
          Trial at Site Level (Phase I)
          Trial at Site Level (Phase II)
          Trial at Site Level (Phase III)
          Trial at Site Level (Phase IV)         [Next]
          Trial at Site Level (Ongoing)
          Trial at Site Level & Growth Rate
          Centers
          Centers and Disease Studied
          Centers and Trial per Center
          Preference Level
          Investigators
```

| ← ⇒ ⟳ | Q | ≡ |

VIS | Location | Center | Investigator      Q Search      About | Account | Help ✉ Contact ▲Arrhythmia   | Find location by city, state, or country |   | Custom Analytics ▼ | | Advanced Center Analytics |

Home > Center > Advanced Center Analytics

| Step 1. > Investigator Criteria | Step 2. > Location Criteria | Step 3. > Center Criteria |

Select Questions >   Step 3.1 > About >    Step 3.2 > Infrastructure >   Step 3.3 > Patients >

| Question | Response |
|---|---|
| 1. Are there any other National regulatory approvals (in addition to the one from IRB/IEC) that you must obtain before enrollment can begin at your location? | Yes ○  No ○  In some cases ○ |
| 2. Are there any other Local regulatory approvals (in addition to the one from IRB/ICE) that you must obtain before enrollment can begin at your location? | Yes ○  No ○  In some cases ○ |
| 3. Is the Local IRB/IEC at your location able to waive authority and use a Central IRB/IEC? | Yes ○  No ○  In some cases ○ |
| 4. What is the average number of weeks required from complete submission until ethics approval (local and/or central IRB/IEC), at your location? | [      ] |
| 5. What is the average number of weeks required from complete submission until regulatory approval, at your location? | [      ] |
| 6. How do ethics submission and regulatory submission processes take place at your location? | Parallel ○<br>Sequential ○ |

[ Next ]

| | | | |
|---|---|---|---|
| ⇐ ⇒ ↻ | 🔍 | | ≡ |

VIS | Location | Center | Investigator | 🔍 Search | About | Account | Help | ✉ Contact ▴Arrhythmia | Find location by city, state, or country | Custom Analytics ▾ | Advanced Center Analytics Home > Center > Advanced Center Analytics

| Step 1. > Investigator Criteria | Step 2. > Location Criteria | Step 3. > Center Criteria |
|---|---|---|
| Select Questions > | Step 3.1 > About > | Step 3.2 > Infrastructure > Step 3.3 > Patients > |

1. Does your center have the capability for evaluating patients with Arrhythmia with the following tests/procedures?

| 1.1 Electrophysiology Study | Yes ○ | No ○ | Can be arranged ○ |

2. Does your center have the capability for evaluating patients with Arrhythmia the following monitoring devices?

| 2.1 In Hospital Telemetry | Yes ○ | No ○ | Can be arranged ○ |
| 2.2 Holter monitoring | Yes ○ | No ○ | Can be arranged ○ |
| 2.3 External loop recorders | Yes ○ | No ○ | Can be arranged ○ |
| 2.4 Postevent recorders | Yes ○ | No ○ | Can be arranged ○ |
| 2.5 Autodetect recorders | Yes ○ | No ○ | Can be arranged ○ |
| 2.6 Implantable loop recorders | Yes ○ | No ○ | Can be arranged ○ |
| 2.7 Real Time Continuous Cardiac Monitoring system | Yes ○ | No ○ | Can be arranged ○ |

[ Next ]

| ← ⇒ C | 🔍 | | | ≡ |

VIS | Location | Center | Investigator     🔍 Search     About | Account | Help | ✉ Contact ▲ Arrhythmia    [ Find location by city, state, or country ]  [ Custom Analytics ▼ ] [ Advanced Center Analytics ]

Home > Center > Advanced Center Analytics

Step 1. > Investigator Criteria | Step 2. > Location Criteria | Step 3. > Center Criteria Select Questions >  Step 3.1 > About >   Step 3.2 > Infrastructure >  Step 3.3 > Patients >

| Question | Category | Answer |
|---|---|---|
| 1. What is the number of Arrhythmia patients in your center database as of July 21, 2014? | | [        ] |
| 2. What is the number of new Arrhythmia patients that enter your center database every month? | | [        ] |
| 3. What is the gender distribution (%) of patients with Arrhythmia in your center database?(should add up to 100%) | Female | [Answer] |
| | Male | [Answer] |
| 4. What is the age distribution (%) of patients with Arrhythmia in your center database? (should add up to 100%) | Under one year | [Answer] |
| | 1-14 years | [Answer] |
| | 15-44 years | [Answer] |
| | 45-64 years | [Answer] |
| | 65+ years | [Answer] |
| 5. what is the proportion (%) of patients with Arrhythmia having the following types as per origin, you see at your center per month?(should add up to 100%) | Atrial | [Answer] |
| | Ventricular | [Answer] |
| | Junctional | [Answer] |
| | Atrio-Ventricular | [Answer] |
| | Unknown | [Answer] |

[ Search Centers ]

| | | | | | | | |
|---|---|---|---|---|---|---|---|
| VIS | Location | Center | Investigator | | Search | About\|Account\|Help✉Contact | |

▲Arrhythmia | Find location by city, state, or country | Custom Analytics ▼ | Advanced Location Analytics Home > Location > Advanced Location Analytics

| Step 1. > Investigator Criteria | Step 2. > Location Criteria | Step 3. > Center Criteria |

No. of Publications | 0-10 | 11-20 | 21-40 | 41-150 | 151-200 | 200-300

FDA Filings | 0-10 | 11-20 | 21-40 | 41-150 | 151-200 | 200-300

FDA Inspections | 0-10 | 11-20 | 21-40 | 41-150 | 151-200 | 200-300

No. of Trials | 0-10 | 11-20 | 21-40 | 41-150 | 151-200 | 200-300

No. of Trials as PI | 0-10 | 11-20 | 21-40 | 41-150 | 151-200 | 200-300

Trial Experience | Phase 1 ◆

[ Next ]

[ Search Investigators ]

| | | |
|---|---|---|
| ⬅ ➡ ⟳ 🔍 | | ☰ |

VIS | Location | Center | Investigator | 🔍 Search | About | Account | Help ✉ Contact ▴Arrhythmia | Find location by city, state, or country | Research Personnel▾ | Advanced Location Analytics Home > Location > Advanced Location Analytics

| Step 1. > Investigator Criteria | Step 2. > Location Criteria | Step 3. > Center Criteria |
|---|---|---|
| Select Questions > Step 3.1 > About > | Step 3.2 > Infrastructure > | Step 3.3 > Patients > |

| Question | Response |
|---|---|
| 1. Are there any other National regulatory approvals (in addition to the one from IRB/IEC) that you must obtain before enrollment can begin at your location? | Yes ○  No ○  In some cases ○ |
| 2. Are there any other Local regulatory approvals (in addition to the one from IRB/ICE) that you must obtain before enrollment can begin at your location? | Yes ○  No ○  In some cases ○ |
| 3. Is the Local IRB/IEC at your location able to waive authority and use a Central IRB/IEC? | Yes ○  No ○  In some cases ○ |
| 4. What is the average number of weeks required from complete submission until ethics approval (local and/or central IRB/IEC), at your location? | [ ] |
| 5. What is the average number of weeks required from complete submission until regulatory approval, at your location? | [ ] |
| 6. How do ethics submission and regulatory submission processes take place at your location? | Parallel ○<br>Sequential ○ |

Next

FIG. 21

| ← ⇒ C | Q | | | ≡ |

VIS | Location | Center | Investigator | | Q Search | About | Account | Help | ✉ Contact ▲ Arrhythmia | Find location by city, state, or country | Research Personnel▼ | Advanced Location Analytics Home > Location > Advanced Location Analytics Step 1. > Investigator Criteria | Step 2. > Location Criteria | Step 3. > Center Criteria Select Questions > Step 3.1 > About > Step 3.2 > Infrastructure > Step 3.3 > Patients >

1. Does your center have the capability for evaluating patients with Arrhythmia with the following tests/procedures?

| | | | |
|---|---|---|---|
| 1.1 Electrophysiology Study | Yes ○ | No ○ | Can be arranged ○ |

2. Does your center have the capability for evaluating patients with the following monitoring devices?

| | | | |
|---|---|---|---|
| 2.1 In Hospital Telemetry | Yes ○ | No ○ | Can be arranged ○ |
| 2.2 Holter monitoring | Yes ○ | No ○ | Can be arranged ○ |
| 2.3 External loop recorders | Yes ○ | No ○ | Can be arranged ○ |
| 2.4 Postevent recorders | Yes ○ | No ○ | Can be arranged ○ |
| 2.5 Auto detect recorders | Yes ○ | No ○ | Can be arranged ○ |
| 2.6 Implantable loop recorders | Yes ○ | No ○ | Can be arranged ○ |
| 2.7 Real Time Continuous Cardiac Monitoring system | Yes ○ | No ○ | Can be arranged ○ |

[ Next ]

FIG. 22

| ← ⇒ C | 🔍 | | ≡ |

VIS | Location | Center | Investigator | 🔍 Search | About | Account | Help | ✉ Contact ▲ Arrhythmia | Find location by city, state, or country | Research Personnel ▼ | Advanced Location Analytics Home > Location > Advanced Location Analytics Step 1. > Investigator Criteria | Step 2. > Location Criteria | Step 3. > Center Criteria Select Questions > Step 3.1 > About > Step 3.2 > Infrastructure > Step 3.3 > Patients >

| Question | Category | |
|---|---|---|
| 1. What is the number of Arrhythmia patients in your center database as of July 21, 2014? | | |
| 2. What is the number of new Arrhythmia patients that enter your center database every month? | | |
| 3. What is the gender distribution (%) of patients with Arrhythmia in your center database? (should add up to 100%) | Female | Answer |
| | Male | Answer |
| 4. What is the age distribution (%) of patients with Arrhythmia in your center database? (should add up to 100%) | Under one year | Answer |
| | 1-14 years | Answer |
| | 15-44 years | Answer |
| | 45-64 years | Answer |
| | 65+ years | Answer |
| 5. What is the proportion (%) of patients with Arrhythmia having the following types as per origin, you see at your center per month? (should add up to 100%) | Atrial | Answer |
| | Ventricular | Answer |
| | Junctional | Answer |
| | Atrio-Ventricular | Answer |
| | Unknown | Answer |

Search Locations

Saudi-Institute

Breast Cancer ▽ | About ▽ | HOSPITAL AGAMENON MAGALACES

Hospital Agamen on Magath Des | Edit Profile | Logout

VIEW PROFILE | Infrastructures ▽ | Patients ▽ | Team ▽ | Expertise ▽ | Research ▽ | Network

ABOUT | GENERAL | BREAST CANCER

How do you characterize your center, by type of practice?
- Public hospital
- University hospital Which patient identification strategies are most commonly used by your center?
- External database (in hospital network)

What is the overhead rate for clinical studies in your center?
- 45%

Which patient recruitment strategies are most commonly used by your center?
- Local recruitment (contact patients in database)
- Local advertisement through postings
- Advertisement in local media
- Direct mailing ◇YES ◇NO ◇POSSIBLY
- Subject cost to participate (mileage, padding, etc.)
- Document archiving or off-site storage
- Recruitment expenses
- Preparation for an audit by the sponsors QA department
- Administrative start-up costs
- IRB related services
- Drafting the informed consent What is the average number of days required for budget and contract execution at your center (round up to closest value)?
- 1-5

| Vis | Location Analytics | Center Analytics | | | | | About | Account ▾ |
|---|---|---|---|---|---|---|---|
| Select disease ▾ | About ▾ | Infrastructure ▾ | Patients ▾ | Team ▾ | Expertise ▾ | Research ▾ | Network |

CENTER ANALYTICS > EDIT PROFILE > NETWORK > BAYLOR PROSTATE CENTER     🖼 View Profile ⟲ Save & Update 🔍 Massachusetts General Hospital, Boston, USA

| Center Name | Trial Collaborations | Contact Last Name | Contact First Name | Contact Email | Invitation Status | |
|---|---|---|---|---|---|---|
| Massachusetts General Hospital, Boston, USA | 10 | Fadem | Stephen | *****@parkhc.co.uk | Accepted | Hide |
| Park Hospital for Children, Portland, USA | 7 | Delgado | Reynolds | ******@mgh.com | Pending | Invite |
| Longhua Hospital, Beijing, China | 5 | Fainstein | Victor | ****@longha.cn | Rejected | Invite |
| Hospital das clinicas, São Paulo, Brazil | 4 | Renato | Victor | ****@longha.cn | Rejected | Invite |

OTHER CENTER YOU MAY HAVE COLLABORATED WITH IN THE PAST

| Center Name | Trial Collaborations | Contact Last Name | Contact First Name | Contact Email | | |
|---|---|---|---|---|---|---|
| Massachusetts General Hospital, Boston, USA | 10 | Fadem | Stephen | ******@parkhc.co.uk | | Invite |
| Massachusetts General Hospital, Boston, USA | 10 | Fadem | Stephen | ******@parkhc.co.uk | | Invite |
| Massachusetts General Hospital, Boston, USA | 10 | Fadem | Stephen | ******@parkhc.co.uk | | Invite |
| Massachusetts General Hospital, Boston, USA | 10 | Fadem | Stephen | ******@parkhc.co.uk | | Invite |

SYSTEMS AND METHODS FOR STREAMING NORMALIZED CLINICAL TRIAL CAPACITY INFORMATION

CROSS-REFERENCE TO RELATED APPLICATIONS

This application is a continuation of U.S. Ser. No. 14/815,425, filed on Jul. 31, 2015, entitled, "SYSTEMS AND METHODS FOR STREAMING NORMALIZED CLINICAL TRIAL CAPACITY INFORMATION" which claims the benefit of U.S. Provisional Patent Application Ser. No. 62/031,492, filed on Jul. 31, 2014, the contents of which are hereby incorporated by reference in their entirety. U.S. Ser. No. 14/815,425, filed on Jul. 31, 2015, entitled, "SYSTEMS AND METHODS FOR STREAMING NORMALIZED CLINICAL TRIAL CAPACITY INFORMATION" is also a continuation in part of U.S. patent application Ser. No. 13/708,154, filed on Dec. 7, 2012, the entire content of which is hereby incorporated by reference in its entirety, which in turn claims the benefit of U.S. Provisional Patent Application Ser. No. 61/569,098, filed on Dec. 9, 2011 and U.S. Provisional Patent Application Ser. No. 61/695,797, filed on Aug. 31, 2012, the entire content of both of which are hereby incorporated by reference in their entirety.

FIELD OF THE INVENTION

Embodiments of the invention relate to qualifying assets for use in clinical trials.

BACKGROUND

Sometimes, when a person is suffering from a life-threatening disease, a drug that would save that person's life has already been discovered by research scientists. However, the government will not approve the drug until it has passed strictly-regulated clinical trials. Those trials typically require double-blind, placebo controlled experiments on thousands of patients.

Planning a clinical trial can take years and millions of dollars. Due to the difficulty in finding qualified research centers, study participants, and investigators, trial planning is very costly. Some attempts to automate the process may not be successful due to the nature of the data involved. Clinical data is sensitive in nature and information that is available in some databases may not be suited for copying, use, or distribution due to privacy restrictions. Additionally, there is such a huge volume of clinical trial data around the globe that it may be a Quixotic task to build a master database of resources. Finally, different data sources use different formats and include different specific data points, which makes it difficult to cross-compare or to work seamlessly with the data from the different sources.

SUMMARY

Embodiments of the invention provide systems and methods that access clinical trial capacity data from different sources and normalize that data into a consistent format that can be queried by a clinical trial planner to pre-qualify different assets for use in a clinical trial. Since the data is streamed from the sources through the normalization process and to the planner, it is not necessary to build a master database and thus the actual technology itself is improved—i.e., for a given server system, a greater number of assets can be pre-qualified in a shorter amount of time since the server system is not required to write all of the data into a database in persistent memory.

System and method embodiments of the invention operate to cause a front-end to be presented to a trial planner (e.g., on a monitor on a computer of the trial planner) and the trial planner can pre-qualify assets such as research centers, locations, and investigators for participation in a prospective clinical trial. It is believed novel to use a tool such as an application programming interface (API) to normalize and merge data relating to clinical trial capacities from different data sources and stream the data to a front-end interface to show assets such as sites, locations, or investigators that qualify for inclusion in a prospective clinical trial according to input criteria established by a clinical trial planner using the system. The system can present a proposed group of assets, streamed through to a planner via a web API, for the planner's consideration. The planner may use the web tool to select criteria for various metrics including ascertaining whether certain assets qualify according to certain questions (either pre-determined in the system or entered on-the-fly), providing tools for filtering for, or querying for certain sites. In general, this provides tools for identifying assets that occupy an optimized sub-space of an N×N space. In a preferred embodiment, N is 3 and the space has dimensions for investigator, location, and site. Investigator, location, and site can each be treated as a unique axis along which to search for qualified assets. Along any given axis, the search, filter, or query process can include ascertaining whether any given assets supplies a specific resource. The system identifies groups of assets that occupy an optimized sub-space of an N×N space. Information about assets may be organized in a disease-specific manner during the normalization and streaming process. Thus, once a planner has selected a disease, queries will only show results that relate to that disease. This provides for focused and efficient search processes. By rapidly pre-qualifying a set of clinical trial assets based on disease-specific competencies, a trial planner can now accomplish in a few key-strokes what previously took months or years or was not able to be performed by data ownership/data warehousing approaches. Since clinical trials can be initiated more rapidly, drugs are brought to market sooner, and suffering is alleviated while lives are also saved. Further, due to the immense cost savings afforded by rapid global site pre-qualification, drug costs are kept low, making more medications accessible to a greater number of people.

In certain aspects, embodiments of the invention provide a process for producing sets of qualified assets for clinical trials by accessing—using an application programming interface (API)—a first online source that provides data about a first set of clinical trial resources, matching a portion of the data to a query by a trial planner relating to a prospective clinical trial, and tailoring the portion of the data to create shareable information describing an asset qualified for the prospective clinical trial. The qualified asset is identified to the trial planner by sending the shareable information from the system to a user computer without storing the data or the shareable information in persistent memory. Preferably the API sends the shareable information by holding the portion of the data only in volatile memory, performing the tailoring in volatile memory, and streaming the shareable information from the volatile memory to the user computer. The process may include accessing a second online source that provides second data about a second set of clinical trial resources and tailoring a portion of the second data to add a description of a second qualified asset to the shareable information. The second asset is identified to the trial planner for the prospective clinical trial by sending the shareable information from the system to a user computer without storing the data or the shareable information in persistent memory. The API may normalize the portion of the data and the portion of the second data into a common format, remove certain identifying details from the data, hold the normalized data in random access memory, or any combination thereof.

The shareable information describing an asset may identify a research site, a geographic location, an investigator, or any other suitable entity. In some embodiments, identifying the assets for the prospective clinical trial (by sending the shareable information from the system to a user computer) includes representing the shareable information using a 3×3 matrix with an axis for each of investigator, site, and location.

Aspects of embodiments of the invention provide a system for planning a clinical trial. The system includes at least one computer processor coupled to a computer memory. The system is operable to receive a query relating to a prospective clinical trial, access a first online source that provides data about a first set of clinical trial resources, and tailor a portion of the data to create shareable information describing an asset for the prospective clinical trial. The system identifies the asset for the prospective clinical trial to the user by sending the shareable information from the system to a user computer without storing the data or the shareable information in persistent memory. Preferably, the system performs the recited steps via a web application programming interface (API) provided by the system. The system may further access a second online source that provides second data about a second set of clinical trial resources and tailor a portion of the second data to add to the shareable information a description of a second asset for the prospective clinical trial. The system identifies, to the user, the second asset for the prospective clinical trial by sending the shareable information from the system to a user computer without storing the data or the shareable information in persistent memory.

In some embodiments, a trial planner can supply a required clinical capacity as linked to a specified disease (e.g., coronary artery disease and catheterization lab; burn unit with helipad; or HIV clinic with inpatient facilities). Moreover, the planner can specify extrinsic preferences or requirements, such as research centers in jurisdictions with a regulatory fast-track or research centers in Asia. Additionally, a trial planner can find centers based on available patient population as indicated by anonymous, aggregated statistical data (e.g., centers with access to patients of a certain ethnicity, centers that historically can recruit more than 100 patients in a month, or centers with access to patients defining a certain age structure).

BRIEF DESCRIPTION OF THE DRAWINGS

FIG. 4 shows a screen for advanced investigator analytics.
FIG. 5 shows an interface for selecting a metric and setting criteria.
FIG. 6 shows filtering for investigators that have addressed a certain question.
FIG. 7 shows a screen for querying for locations.
FIG. 8 shows a screen for querying for sites.
FIG. 9 shows a screen for querying for investigator patient availability.
FIG. 10 gives a screen for creating a group of investigators.
FIG. 11 shows an interface for selecting a metric and setting criteria for an investigator.
FIG. 12 shows or selecting a metric and setting criteria for a location.
FIG. 13 shows filtering for sites that have addressed a certain question.
FIG. 14 is a screen for filtering or querying sites.
FIG. 15 is a screen for querying sites about certain resources.
FIG. 16 is a screen for querying for sites based on patient availability.
FIG. 17 gives a tool for creating groups of sites.
FIG. 18 shows a home screen for selecting metrics and setting criteria for locations.
FIG. 19 shows selecting a metric for locations.
FIG. 20 shows filtering for locations for which a certain question has been addressed.
FIG. 21 illustrates filtering locations by questions.
FIG. 22 gives an infrastructure screen.
FIG. 23 presents a tool for advanced location analytics.
FIG. 26 shows a part of a center profile according to certain embodiments.
FIG. 28 shows an exemplary screen for editing a network.
FIG. 29 shows a screen for inviting an entity to join a network.

DETAILED DESCRIPTION

Figure 1:
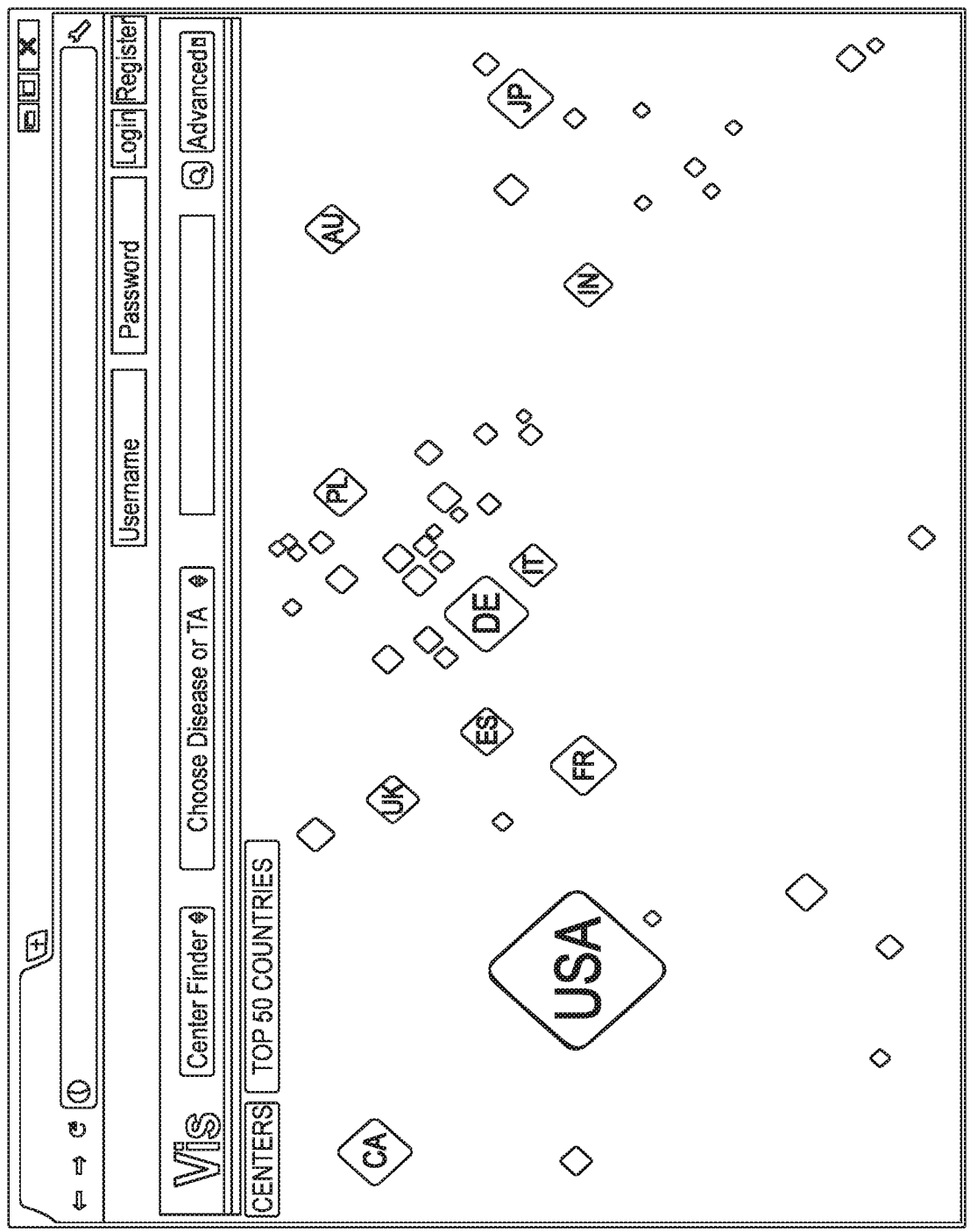
FIG. 1 shows a display of locations where clinical trial centers are located.

Embodiments of the invention provide systems and methods by which a clinical trial planner can pre-qualify assets such as sites, locations, or investigators for participation in a prospective clinical trial. Embodiments of the invention use a tool such as an API to access data from multiple sources and create a "mashup" by normalizing the data and merging them into a single stream queryable by the trial planner. This provides tools for viewing and analyzing a global network of assets by general and disease-specific parameters relating to regulatory environments, candidate patient populations, and clinical capacities as well as center and investigator competencies as demonstrated through factors such as past trials, publications, and collaborative abilities. For the trial planner, embodiments of the invention generally provide tools for site selection during the planning of a clinical trial. Using tools of embodiments of the invention, a trial planner can view lists of assets such as research centers, locations, and investigators, or information about individual assets to assist in identifying those assets that are viable candidates for inclusion in the planned trial. Further, embodiments of the invention provide tools by which a trial planner can, having in mind one or more criteria for participating assets in which those criteria are general or disease-specific, identify assets that satisfy the planner's criteria.

Normalization (i.e., normalizing the data) is a process that facilitates a data aggregator to combine information from multiple sources while accounting for underlying differences in how the data had been gathered. Normalization may take place on either the source side or the aggregator side of a data interface between source and aggregator. For example, if a source (e.g., a sponsor) desires to keep secret (i.e., not reveal) the sample size of various studies, the source may normalize the data in order to transform the data into a metric that is independent of study size, e.g., by reporting data in terms of percentiles rather than raw counts, or by reporting data on a logarithmic scale relative to a reference value, or to adjust for patient characteristics such as age, etc. Statistics of the data may also be reported (e.g., mean values, standard deviations, statistical confidence values, rank or ordinal value, etc.). Raw counts or raw data are not necessarily reported. Normalizing data at the source still allows for conclusions and inferences to be drawn from the data, but without necessarily revealing the raw data itself.

Alternatively, a data aggregator may normalize data after receiving raw data from the source along with relevant conditions on the data. Normalizing by the data aggregator may facilitate making sure that compatible data is combined (e.g., an apples-and-apples combination rather than an apples-and-oranges combination).

At level of a trial planner, normalization before data sharing may involve gathering information prior to sharing it. The gathered information may then be indexed, transformed to another scale (e.g., log scale, percentile, ordinal value, etc.) to produce one or more metrics, and then sharing the one or more metrics. The actual values of the raw data is not shared. For example, data from different relative scales can then be aggregated with other similarly-scaled data. Embodiments enable the sharing of insights, inferences or index information without sharing the data itself.

Normalization may include usage of an identification (ID) number to match related data across disparate systems. For example, suppose that data for a doctor is reported from various sources (e.g., multiple hospitals where the doctor may have privileges, the doctor's clinic, etc.). If it is important that aggregated data be generated on a per-doctor basis, the normalized data may include a doctor ID number so that only data that share a doctor ID number are combined. The ID number allows for other attributes of the doctor to be intentionally hidden or obscured.

Embodiments of the invention include the recognition that at present and in recent years, an ever-increasing percentage of clinical trials are multi-site, multi-national trials and that existing approaches to trail planning are unmanageable. In some embodiments, tools of embodiments of the invention allow a trial planner to analyze and evaluate assets according to specific criteria, capacities, performance indicators, benchmarks, or intrinsic or extrinsic aspects of the center and its location.

Compared to prior art approaches that required paper-based feasibility questionnaires, embodiments of the invention provide a system for applying criteria relevant to a prospective clinical trial to the universe of research centers to identify those centers that pre-qualify for participating in a study.

Embodiments of the invention include the recognition that at present and in recent years, an ever-increasing percentage of clinical trials are multi-site, multi-national trials and that existing feasibility-questionnaire-based approaches to trail planning not only require very large amounts of money to be spent to plan a trial—thus keeping smaller firms from sponsoring studies and bringing new drugs to market—but also consume large amounts of time, delaying the entry of life-saving drugs to market. System and method embodiments of the invention are provided to reduce cost and time, while increasing the quality of trial plans coming out of the trial planning process. Embodiments of the invention include the recognition that significant barriers exist to effective trial planning in the form of uncertainty about foreign and international regulatory approval processes. For example, where a firm in the Americas or Europe may seek to plan and sponsor a trial for a new drug, there may be uncertainty about applicable rules and regulations in China, Taiwan, Korea, Indonesia, Hong Kong, Singapore, or India. Tools of embodiments of the invention aid sponsors in establishing and building productive relationships with contract research organizations (CRO)s or centers in various international markets. In some embodiments, tools of the invention allow a trial planner to analyze and evaluate centers according to specific criteria, capacities, performance indicators, benchmarks, or intrinsic or extrinsic aspects of the center and its location Clinical trials are discussed in Potter, et al., Site selection in community-based clinical trials for substance abuse disorders: strategies for effective site selection, Am J Drug Alc Abuse 37:400-407 (2011); Ng, R., Drugs From Discovery to Approval, 2d Ed, 2000, John Wiley & Sons, Hoboken, N.J., 466 pages; Chung, et al., A guide on organizing a multicenter clinical trial: the WRIST study group, Plast Reconstr Surg 126(2): 515-523; and Rohrig, et al., Sample size calculations in clinical trials, Dtsch Arztebl Int 107(31-32):552-556 (2010), the contents of each of which are incorporated by reference herein in their entirety for all purposes.

Certain embodiments of the invention provide an API for querying extrinsic databases for assets and tools for querying across multiple axes that include general information as well as disease-specific information. Moreover, one hallmark of embodiments of the invention is the ability to present subsets of the total profile of information organized by disease.

Within a disease-specific asset set, a trial planner can view numerous specific pieces of information relevant to the capacity of those assets to participate in a clinical trial. For example, a planner may wish to plan a trial that includes 500 patients representing individuals of both Asian and European ancestry. The trial planner may wish to use centers that are in jurisdictions with regulatory fast tracks and in which clinical trial preparatory stages can run simultaneously (e.g., regulatory approval and patient recruitment) and not sequentially. The trial planner may need a certain percentage of the patients to have a disease such as, for example, lung cancer. Finally, the trial planner may wish to only include centers with the capacity to perform the tumor M2-PK EDTA plasma test, the serum carcinoembryonic antigen (CEA) test, and the tissue inhibitors of matrix metalloproteinases-1 (TIMP-1) test. Using tools of embodiments of the invention, the trial planner can input those parameters and receive a list of centers, locations, or investigators that satisfy the criteria.

Certain aspects of embodiments of the invention provide novel tools that normalize data to deal with data sharing concerns. A tool such as an API provides for integrated search based on third party data from different sources while overcoming data sharing concerns. The output from the API tool can be an optimized list of investigators, centers, and locations based on aggregated data from multiple sources. The API facilitates real-time pooling of data in ways that would otherwise be impossible (e.g., based on local database models).

Using tools of embodiments of the invention, the trial planner can input those parameters and receive a list of centers. The trial planner can then view a profile for each center to further evaluate the center for possible inclusion in the study.

In some embodiments, a trial planner may need to ascertain some fact about the centers that is not already included in their profiles. Tools of embodiments of the invention can accept a question from the planner (e.g., "Do you have next generation sequencing (NGS) hardware?") and relay it to center personnel. Answers may be integrated into the knowledge base to be queryable in subsequent uses of system embodiments of the invention. Thus, embodiments of the invention allow a trial planner to drive the development of the underlying knowledge base by proposing new questions for inclusion into the data gathered from center personnel (which is discussed in greater detail below).

Further, while system embodiments of the invention can provide and display lists or groups of qualifying centers and profiles of individual centers, including profiles that are composed to represent the capacities of the center in general, as well as the capacities of the center as regards a specific disease, embodiments of the invention also provide tools for provision of profiles of individual investigators working in connection with the centers. As discussed below, embodiments of the invention include tools and mechanisms by which individuals can contribute to or edit their profiles, including mechanism for pre-populating profiles automatically and allowing individuals to confirm or edit the pre-populated content.

In certain aspects, embodiments of the invention provide novel tools for the display of global networks of research centers to provide a valuable, powerful, and intuitive visualization of research center capacity.

FIG. 1 shows a display of locations where clinical trial centers are located according to certain embodiments of the invention. The embodiments provide visual information systems functionally linked to profiles and sets of profiles. Information relevant to centers is delivered as a dynamic visual display, which can receive interaction from a user in the form of touchscreen, keyboard, or mouse gestures while composing a profile of a research center, or a group of research centers, or a map-view of research locations, in response to that interaction. For example, as a user types "P", then "a", a display will offer "Palo Alto," "Paris," and similarly-named places. When the user chooses one, the screen displays research locations from those places in a map-view. A research location can include a research center, or a geographic location of one or more research centers. Map views of embodiments of the invention are functionally linked to profile information. A user can position a particular map view on-screen, and further specify a disease. The display screen can adjust the links to profiles of research centers within the present map-view that have performed a clinical trial relevant to that disease. If a user changes the disease to a second disease, the display can change in functional response to the user's input, displaying links to profiles of research centers that have performed clinical trials relevant to the second disease.

Against a background of such an exemplary front-end interface, tools of embodiments of the invention can provide for integration of data from outside data source with each other and/or with data stored locally in a database. The web API normalizes data from outside sources in any of a number of ways so that data is suitable for sharing and that data from disparate sources may be integrated. In some embodiments, normalizing data includes one or more of: performing a mathematical normalization on values so that raw counts are reported as percentages; removing certain source-specific detail so that data from the extrinsic source matches an internal standard; removing certain data the inclusion of which would be prohibited under the data privacy laws of some certain jurisdiction; reformatting data (e.g., streaming data in from an external source in data normal format and populating an XML document with the data points); others; or a combination thereof.

Thus, system embodiments of the invention provide valuable tools for the evaluation of research centers for inclusion in particular clinical trials. Certain embodiments of the invention offer a multi-axis system for clustering research centers. The system can include one or more of: an axis for geographic location; an axis for disease; an axis for extrinsic characteristics; and an axis for an intrinsic characteristic. Each research center can optionally have at least one value along each axis. A user can select values along N different axes (e.g., Asia, autism, available population of subjects under age 14, publication in a journal with impact factor >25, indirect costs <30th percentile). It should be noted that the disease selection can further optionally define additional axes in combination with primary axes. Thus system embodiments of the invention can combine autism with publication to query for "publications on autism in a journal with impact factor >25". The selection of values (along with an optional plus/minus range) defines an N-dimensional space including certain research centers. System embodiments of the invention can collocate information relevant to those centers and optionally the chosen disease and other axis values, and use the collocated information to compose—for example in response to a user interaction—a profile for each of one or more of those research centers. The profiles can be displayed in relation to how the user interacts with the system. The profiles can optionally be stored (e.g., for later viewing or downloading, optionally in connection with a user's login or account). Sets of research centers can be defined by a particular defined N-dimensional space, and those sets can comprise geo-graphically segregated subsets. A set can be offered to the user, e.g., for display in the interactive visual system of embodiments of the invention, or as a list or similar data file, or can be offered for sale to the user, to be provided in a display or file.

System embodiments of the invention include a database accessible through client devices over internet connections. Embodiments of the invention provide tools for meaningful review and use of the data. Some embodiments of the invention provide HTML5 based interaction tools. Embodiments of the invention further provide advanced search algorithms to enable a user to find research centers that can fulfill trial-specific needs. The user may, for instance, filter the center search by disease, location, local cost per patient, local availability of specific comparator drug, local acceptance of placebo-control, size of local patient sub population, or availability of a certain diagnostic tool or expertise in the research center. Embodiments of the invention provide tools for screening research centers, or including them in result sets, based on criteria including aspects related to: research personnel, patient population, research infrastructure, cost, research activity, regulatory environment, publication history, peer reviews or ratings, or expertise areas.

Embodiments of the invention provide tools for maintaining, composing, rendering, and displaying profiles of research centers and further provides for disease-specific profiles, allowing for more than one profile per center. Users can easily move back and forth between analysis of disease-specific capabilities of the centers and global comparisons of locations of interest. Embodiments of the invention provide a live integration whereby information included within a profile component influences live geo-referenced visual displays of research entity information. This aspect of embodiments of the invention provide research facilities with an incentive to contribute information into profile components, thereby increasing the value of the visual displays to research planners.

Embodiments of the invention provide a user with information identifying assets for a proposed clinical trial. An asset may be a site, location, investigator, or other suitable entity. As used herein, "site" may be taken to refer to a research center or an institution at which a clinical trial can be conducted. As used herein, "location" can be taken to refer to a geographic area such as a city, a postal code, a country, a continent, a recognized geographical entity such as the pacific-northwest, eastern Europe, or the south. An investigator is generally a medical professional who conducts clinical trials. It will be recognized that these assets each in their own way represents one tool for gaining access to suitable resources such as an available patient population. By aggregating data from previous trials or other available sources, embodiments of the invention can provide patient population information which can be used similarly to, but more freely than, patient population gathered through methods that rely on patient-specific or patient-identifying information, as this data includes of information that does not identify individual patients. Embodiments of the invention provide systems and methods to aid trial planners in identifying assets that would be qualified for a prospective trial, which can be used where use of patient-identifying information is otherwise prohibited. In particular, in combination with the disease-specific modality of embodiments of the invention, a trial planner can access complex, multi-dimensional data previously unavailable and critical to planning an effective clinical trial.

Figure 2:
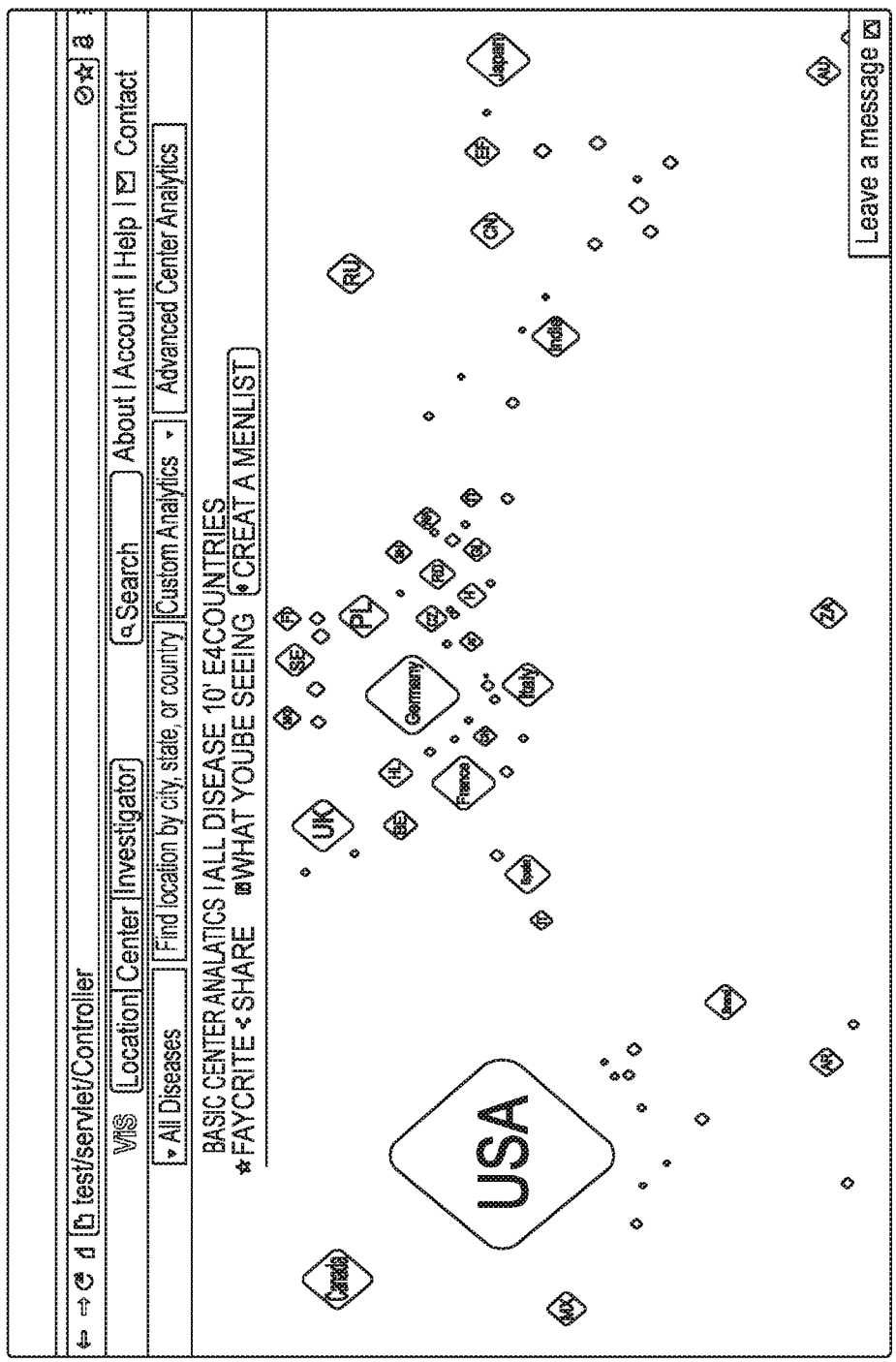
FIG. 2 shows a screen for advanced center analytics.
Figure 3:
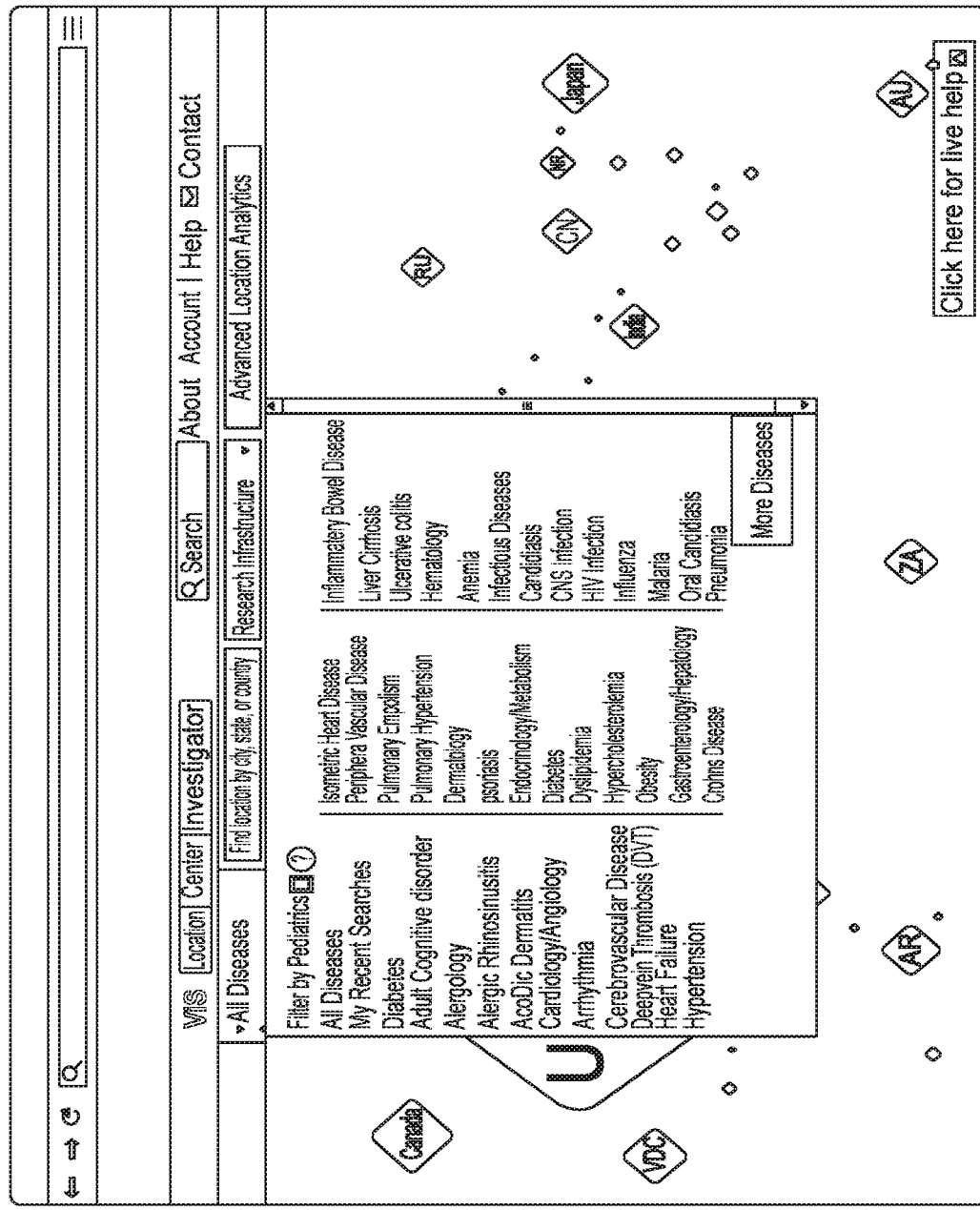
FIG. 3 shows a screen for advanced location analytics.

FIG. 2 shows a screen for advanced center analytics and FIG. 3 shows a screen for advanced location analytics while FIG. 4 shows a screen for advanced investigator analytics. It can be noted that interfaces of embodiments of the invention establish an N×N search matrix in which a planner can optimize values for variables in N spaces. In the depicted embodiment, N is 3 with one axis for location, one axis for investigator, and one axis for site. A planner can select critical metrics for each category of asset (i.e., each axis) and set criteria for those metrics.

FIG. 5 shows an interface for selecting a metric and setting criteria. Additionally, a planner can optimize sets of assets within the N×N space using the concept of asked-and-answered questions to establish groups.

Figure 6:
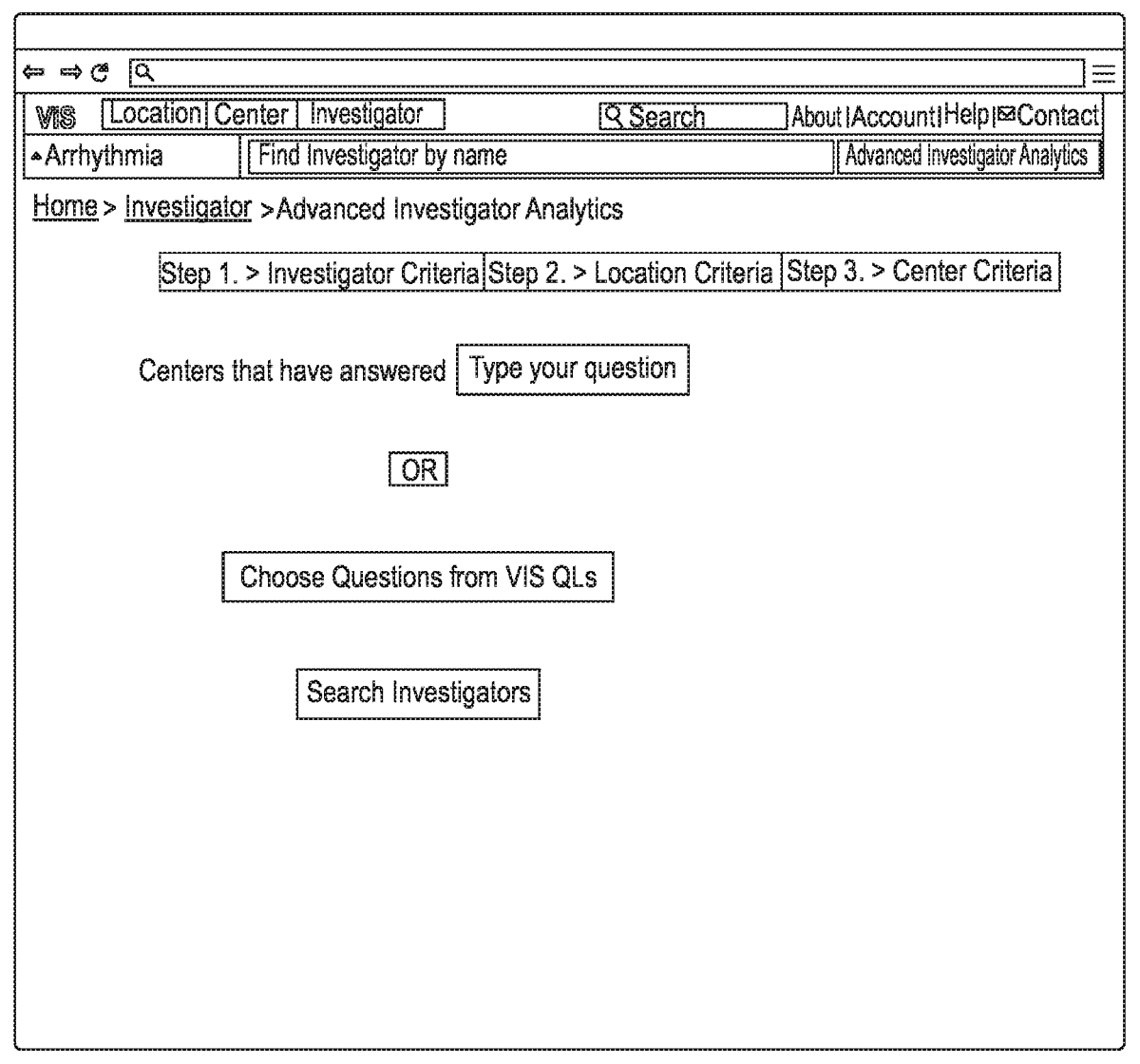

FIG. 6 shows filtering for investigators that have addressed a certain question. FIG. 7 shows a screen for querying for locations. FIG. 8 shows a screen for querying for sites. FIG. 9 shows a screen for querying for investigator patient availability. In each of FIGS. 6-9, a planner can establish search parameters along one of the axes. In API-based embodiments, the API can use the established parameters when normalizing extrinsic data to cull all of the prospective assets to arrive at a narrower set of defining a group of assets satisfying the planner's criteria.

Figure 10:
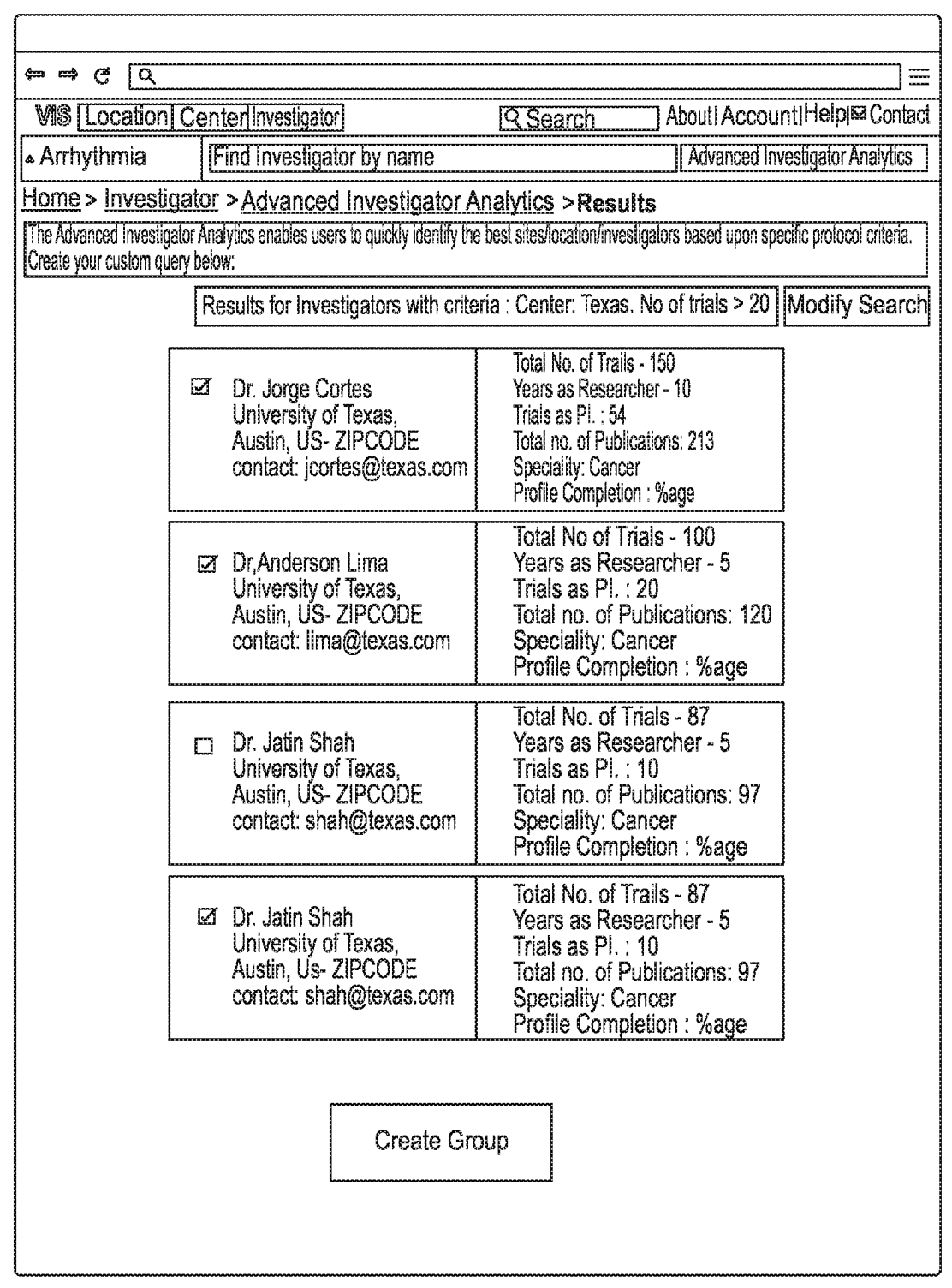
Figure 11:
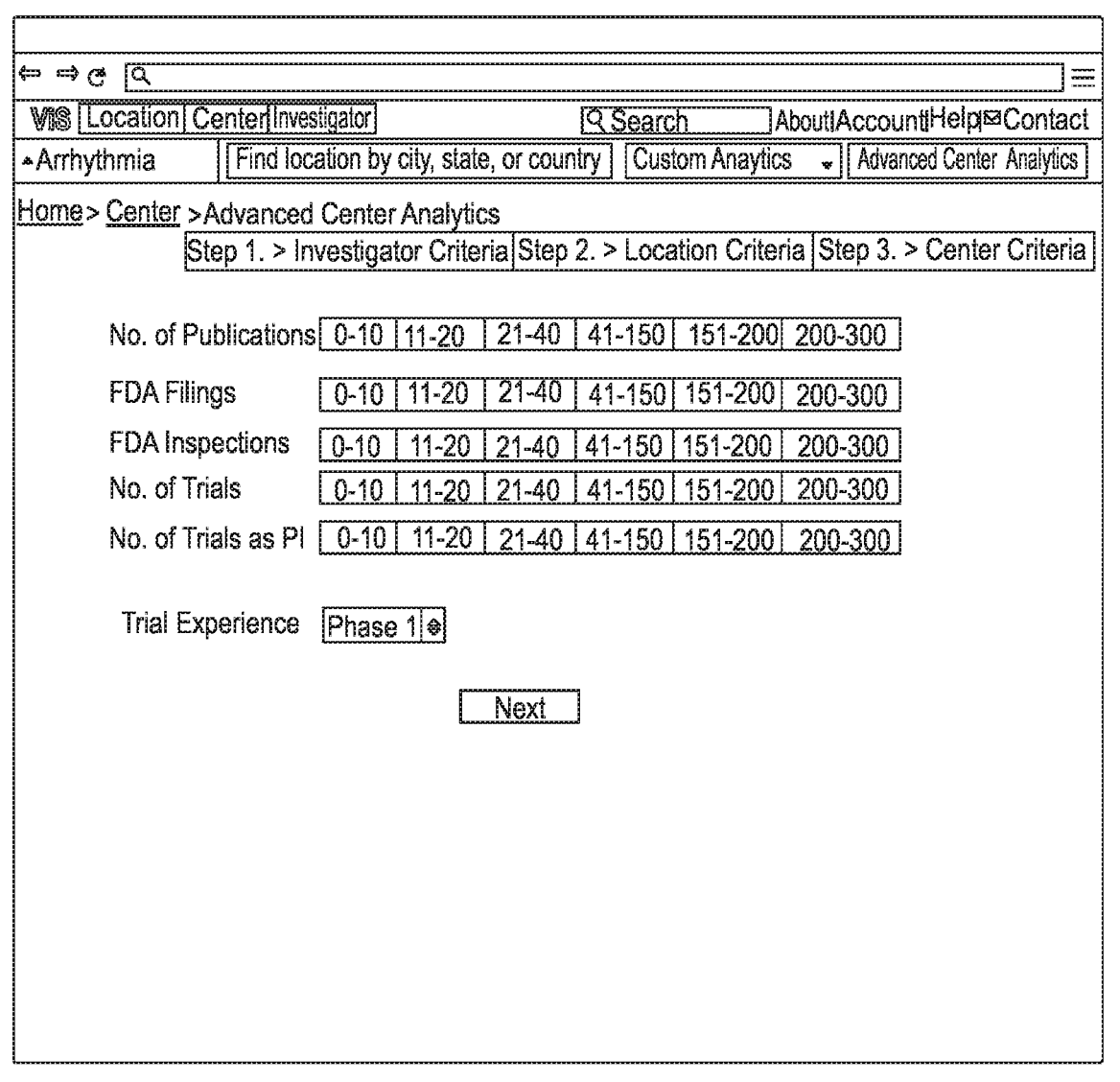
Figure 13:
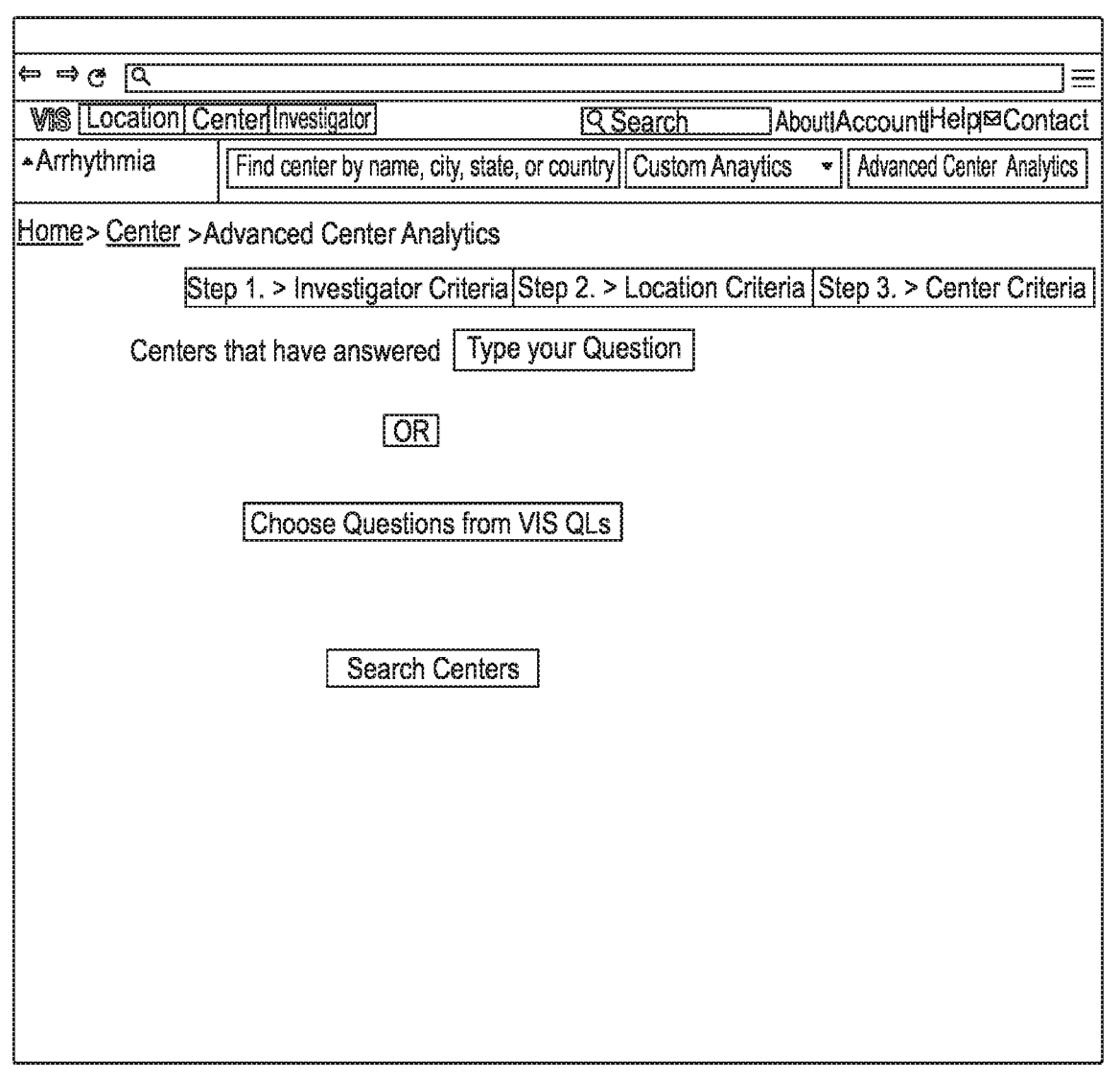

FIG. 10 gives a screen for creating a group of investigators. In the illustrated example, the screen has presented a proposed group of assets (here, investigators), streamed through to the planner via a web API, for the planner's consideration. A planner may use the web tool to select criteria for various metrics including ascertaining whether certain assets qualify according to certain questions (either pre-determined in the system or entered on-the-fly), providing tools for filtering for, or querying for certain sites. In general, this provides tools for identifying assets that occupy an optimized sub-space of an N×N space. In a preferred embodiment, N is 3 and the space has dimensions for investigator, location, and site. FIG. 11 shows an interface for selecting a metric and setting criteria for an investigator. FIG. 12 shows or selecting a metric and setting criteria for a location. FIG. 13 shows filtering for sites that have addressed a certain question. FIG. 14 is a screen for filtering or querying sites. Thus it can be seen that investigator, location, and site can each be treated as a unique axis along which to search for prime assets.

Along any given "axis", the search, filter, or query process can include ascertaining whether any given assets supplies an specific resource. For example, pieces of medical equipment can be specified, patient availability can be specified, or any other variable or feature of interest can be specified. FIG. 15 is a screen for querying sites about certain resources. FIG. 16 is a screen for querying for sites based on patient availability. The system identifies groups of assets that occupy an optimized sub-space of an N×N space.

Figure 17:
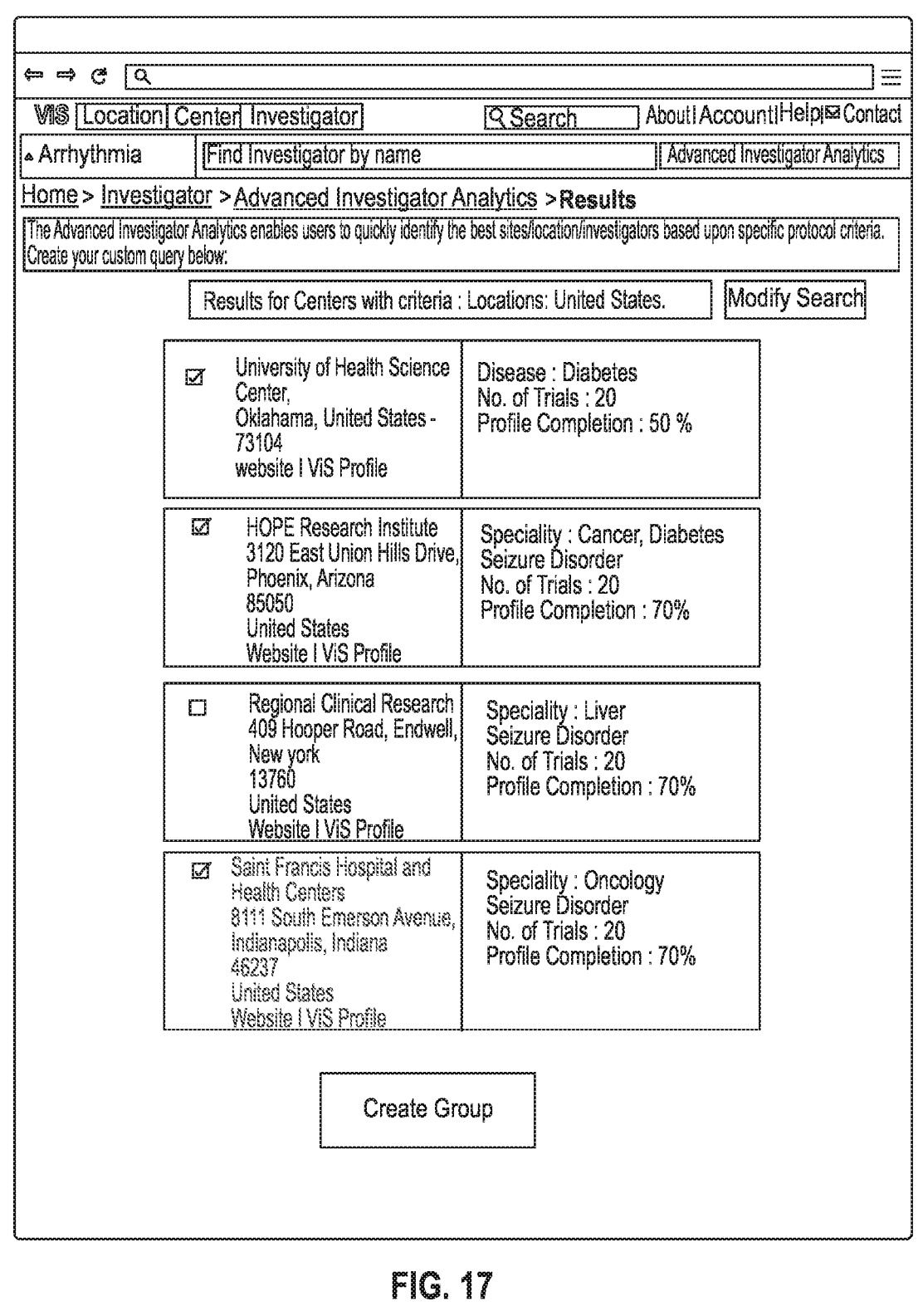
Figure 19:
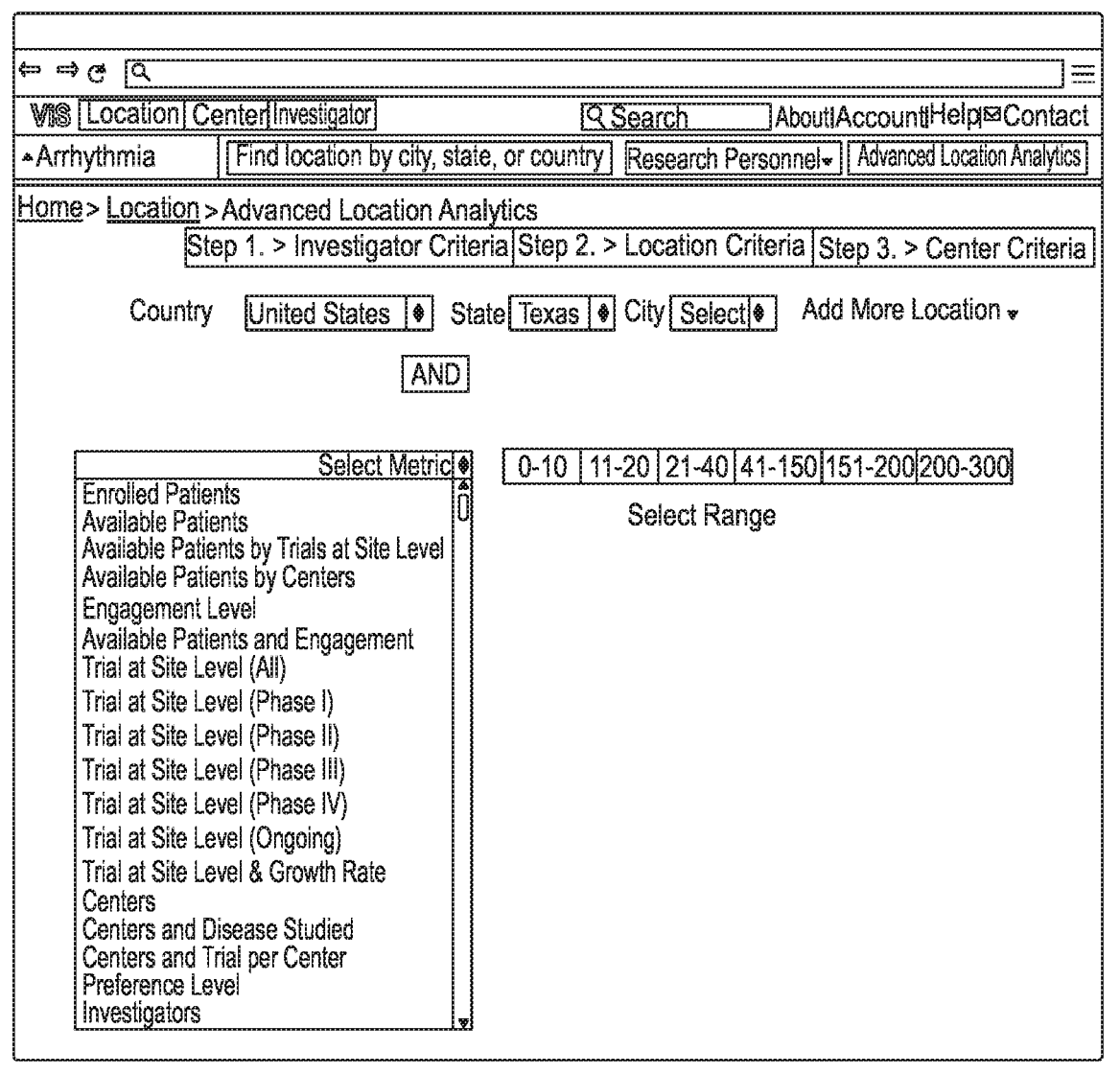
Figure 20:
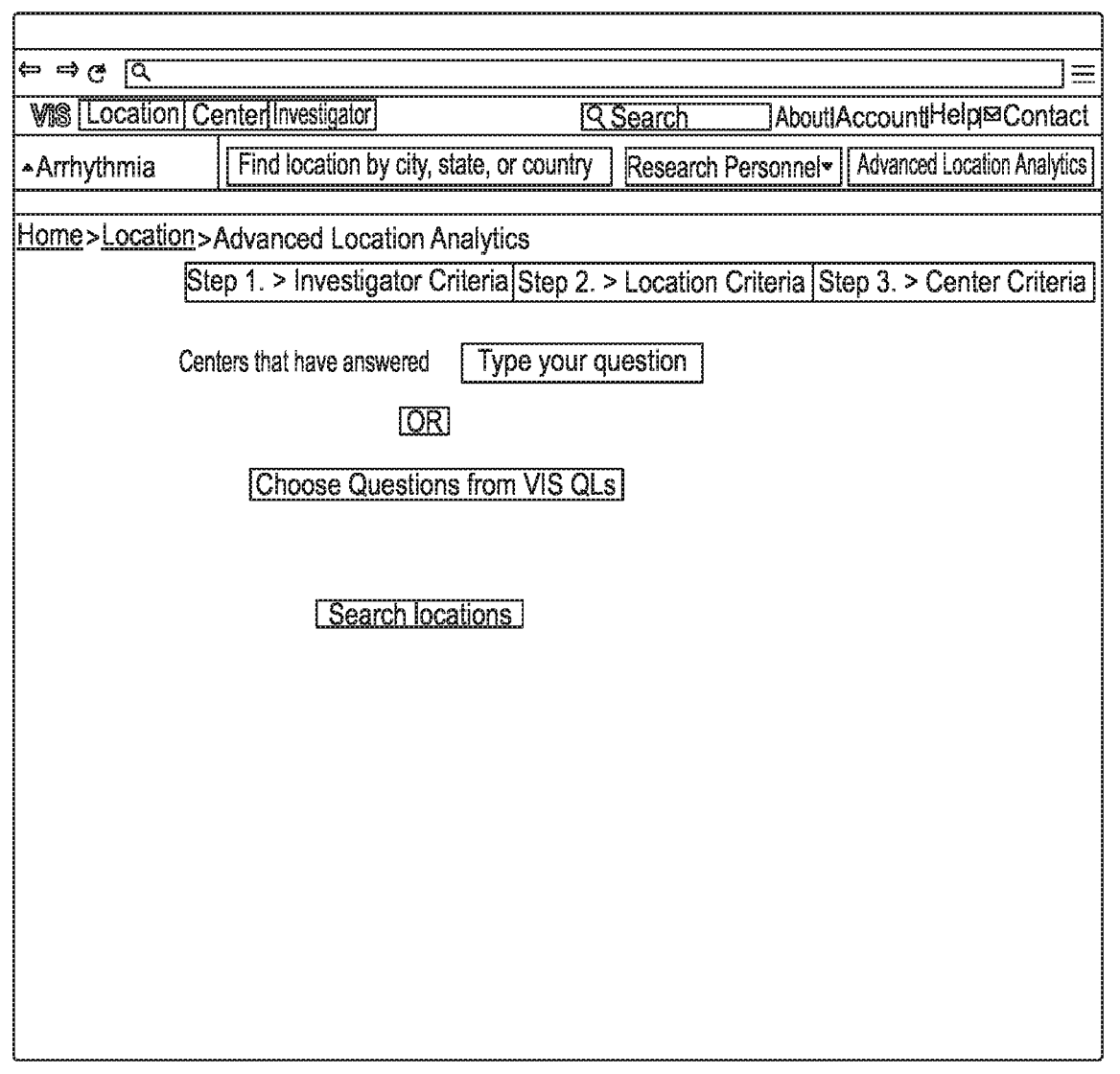

FIG. 17 shows an interface providing a group of assets—here, sites—at which a planner can select and "lock-in" a group of interest. FIGS. 18-23 shows various screens that a planner can interact with to arrive at the optimized group of assets. Remembering that an asset can be, for example, a location, a site, an investigator, or a network, querying against one of those assets can be done to provide or narrow results within a different category of assets. Thus a planner looking for sites can query by location. In looking for certain locations, a planner can provide filters that are applied to sites. In looking for locations or sites, a planner can select metrics and set criteria for investigators (or for sites, locations, or any combination of investigators, sites, locations, networks, etc.). FIG. 18 shows a home screen for selecting metrics and setting criteria for locations. FIG. 19 shows selecting a metric for locations. A planner can use questions to limit and optimize assets that are included in result groups. FIG. 20 shows filtering for locations for which a certain question has been addressed. FIG. 21 illustrates filtering locations by questions. As previously discussed, a planner can require or query for certain infrastructure. For example, in searching for assets by space in a 3×3 matrix a planner can search for assets for which sites have certain infrastructure, locations are characterized by certain patient populations, investigators with certain credentials or network strengths, or any combination thereof. FIG. 22 gives an infrastructure screen. FIG. 23 presents a tool for advanced location analytics. Having specified these criteria, systems and methods of embodiments of the invention provide the planner with identified assets—such as prime locations for a clinical trial—that meet the planner's needs.

Figure 24:
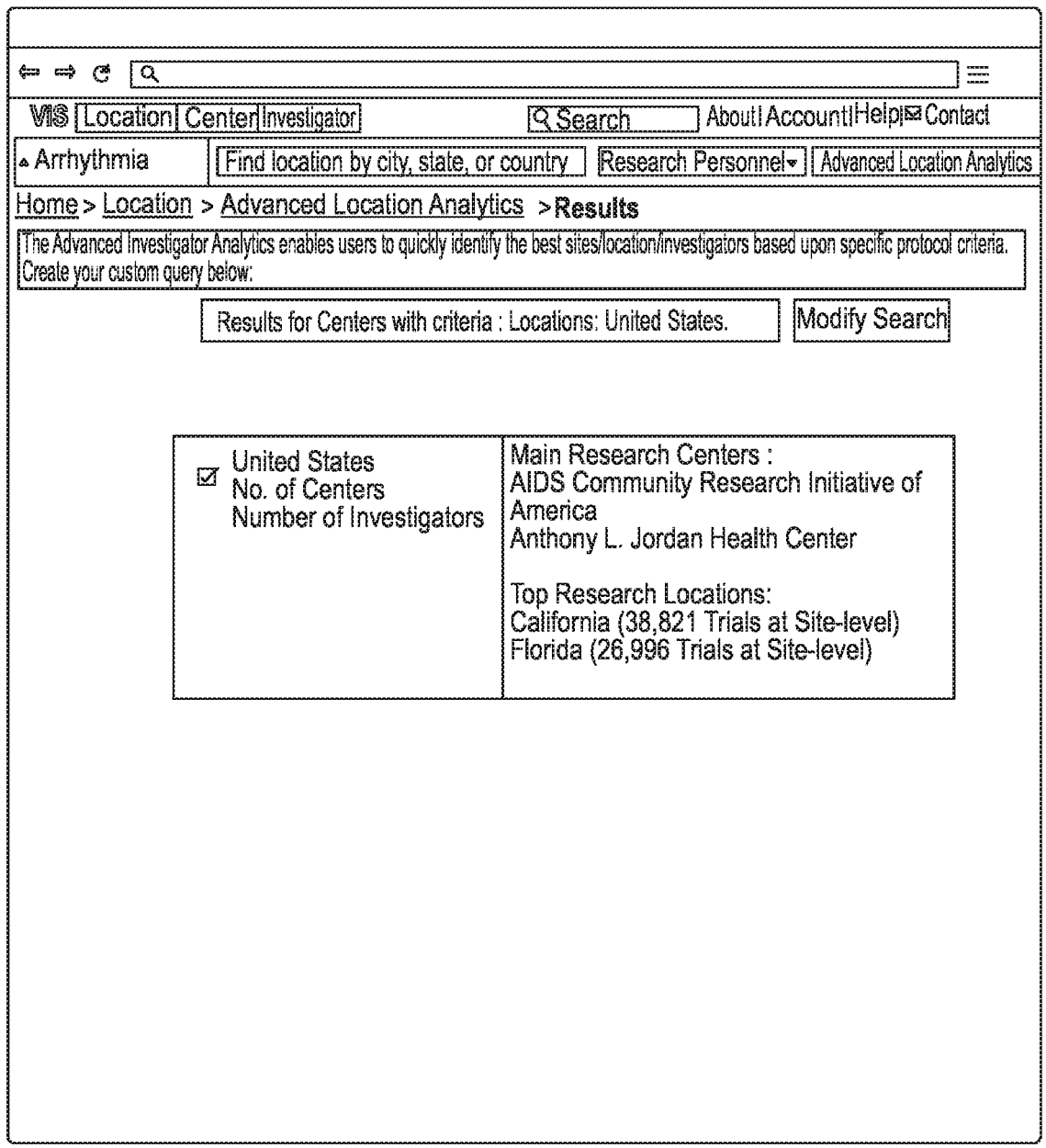
FIG. 24 shows the selection of a location.

FIG. 24 shows the selection of a location.

Furthermore, embodiments of the invention provide robust tools for the critical evaluation of assets individually or for the synthesis of groups of assets according to critical evaluation standards chosen by a user. By including data known by the industry to be indicative of the performance of an asset of interest to a trial planner, tools of embodiments of the invention can be queried for one or more relevant critical values in one or more relevant metrics (such as, location, cost, the user's prior subjective evaluation, local government's rules (i.e., participate in PCT? Informed consent laws similar to country X? last inspection date?), or center administration (non-profit? Owned by company Y? publically traded on NYSE? Professional staff member-in-good-standing of association?). Thus, a planner of a clinical trial has access to valuable information defining research centers across the globe, allowing the planner to identify and evaluate centers, for example, for potential participation in clinical trials.

Embodiments of the invention provide the ability to offer certain output components free of charge while offering other output components for a fee, thereby deriving revenue from research planners who benefit from the embodiments. Methods and systems of embodiments of the invention are optimized to collect or aggregate highly specialized human expertise that is very hard to replicate, combined with vast amounts of information and complex algorithms that are tightly protected as trade secrets. Embodiments of the invention include displays and visualizations that are used to provide results such as sets of assets to a user. Visualizations according to embodiments of the invention are discussed in U.S. Pub. 2013/0151275, incorporated by reference, the text of which publication is not being repeated here in full. Embodiments of the invention provide methods for rendering a display of one or more elements. Elements can represent entities that exist, for example, in the natural world or in a data set corresponding to a world (e.g., a game world or a file showing plans for future buildings). Each element can be positioned within a display (e.g., a screen) according to the relative position of an associated entity. The display can be re-rendered to correspond to different levels of magnification (i.e., different levels of zoom).

Visualizations

Some aspects of the invention generally relate to systems for displaying information relevant to one or more entities. FIG. 1 is one display according to an embodiment of the invention. Certain system embodiments of the invention reference the geo-coordinates of a number of entities. The entities can be, for example, clinical research centers or facilities. The system composes output suitable for display by a client application.

A client application according to embodiments of the invention can be web browser, and the system can compose HTML5. In some embodiments, the client application is a standalone "app", for instance, that a user installs onto a device, and the output is proprietary code capable of being interpreted by the app. In other embodiments, the output is flash animation. In some embodiments, the output is a JavaScript command.

In some embodiments, a display is interactive. Possible interaction include: zooming; panning; rotation; and clicking or tapping an element. A display can be rendered on a touch screen device or through any computer monitor including, for example, LCD projectors. On a touch screen device, interactions include pinch-to-zoom or swipe-to-pan or any other gesture-based interactions known in the art. On a computer monitor, interaction can be done through a mouse or other pointing device, and can include, for example, zooming by use of a scroll-wheel, panning by mouse-swipe, and clicking to activate a link. Any such means for receiving client interaction data are included in embodiments of the invention.

A display according to embodiments of the invention generally includes one or more elements, shown in FIG. 1 as convex polygons having the form of equilateral diamonds. In certain embodiments, the elements are tessellating figures (e.g., squares, diamonds, hexagons, hexagons and pentagons in about a 20:12 ratio, irregular figures, Escher lizards or other whimsical figures, etc.).

Each element is associated with one set of geo-coordinates. Depending on the level of "zoom", a set of geo-coordinates can be associated with one entity or a cluster of entities. For example, at a very "zoomed in" level, a display area may correspond to a city or neighborhood, and each entity will have a set of geo-coordinates comprising one latitude-longitude pair. At a more "zoomed out" level, a display area may correspond to a country, and all entities that are in a city may have their geo-coordinates put into a set that corresponds to a single display element. At the most zoomed-out level, for example, each display element may correspond to a nation, and all entities within that nation may be represented by that display element.

In certain embodiments, an aspect of a display element indicates a number of entities associated therewith. As illustrated in FIG. 1, USA is the largest display element and thus includes the most research facilities. Japan (JP) is a mid-sized element, and thus includes an intermediate number of facilities.

To display elements, embodiments of the invention provide for receiving the associated geo-coordinates (i.e., pulling them from a database, from mapping or GIS program, or receiving them as input) and translating the geo-coordinates into computer-readable code capable of being rendered in a display. For the sake of convenience, since that computer-readable code includes a representation of the relative position of the elements, that code can referred to as translated coordinates. Translated coordinates can refer to information to position an element on a screen and is not limited to a pair of latitude and longitude numbers (although those are included in certain embodiments).

In some embodiments, system and method embodiments of the invention receive display elements, not as coordinates, per se, but as elements rendered or delivered as displayable data. For example, elements can be present as scalable vector graphics, or can be rendered by a software program or service. In some embodiments, the coordinates of elements take the form of a drawing command issued to an Application Programming Interface (API), and a transformation of those coordinates takes the form of a new command. System and method embodiments of the invention can receive information for displaying elements in many formats, including but not limited to: SVG 1.1 (second edition), GPX (a standard format used with many devices and programs, including Garmin's eTrex, GPSMAP, Oregon, Dakota, Colorado, & Nüvi series), Google Earth (.kml/.kmz), Google Maps routes (URLs), Geocaching.com (loc), XML feeds, Garmin Forerunner (.xml/.hst/.tcx), Timex Trainer, OziExplorer, Cetus GPS, PathAway, cotoGPS, CompeGPS, TomTom (.pgl), IGN Rando (.rdn), Suunto X9/X9i (.sdf), and tab-delimited or comma-separated text. The digital form by which displayable elements are delivered to or handled by embodiments of the invention is described as coordinates for convenience's sake, as it is acknowledged that SVG, etc., can describe elements that are intuitively or satisfactorily analogized to coordinates. In some embodiments, a program (i.e., PHP script) converts among SVG files, geo-coordinates, drawing commands for a JavaScript API, and similar. In some embodiments, elements include objects of types such as GMarker, GIcon, GPolyline, GTileLayerOverlay, GInfoWindow, or similar, which can be interpreted, for example, by a JavaScript API (e.g., version 3 of the maps JavaScript API). In some embodiments, elements are displayed in a standalone app or by tools such as Rails with, for example, an app made with the Rails plug-in Geokit.

While elements are described herein as having coordinates, which can be transformed or adjusted, such descriptions include processes of rendering pixels and, for example, subsequently re-rendering pixels to "overwrite" the first set, or to give the impression of animation. For effective communication, elements are described in terms of coordinates, and adjusting or moving those elements, or displays thereof, can be described as transforming the coordinates. In some embodiments, transforming coordinates involves re-drawing a visual display. In some embodiments, transforming coordinates involves re-issuing a drawing command, causing an API such as a JavaScript API to redraw a screen.

A display element of embodiments of the invention generally includes an area of a display and therefore includes more than a point. A pair of geo-coordinates generally indicates a point. Accordingly, translation of geo-coordinates according to embodiments of the invention includes creating digital data that describes an area of a display (e.g., a specified plurality of pixels on a monitor). Thus, translated coordinates can be described as a set to the extent that, when a display area is considered as a field of contiguous unit areas (e.g., like pixels on a monitor), translated coordinates encompass a number of the contiguous unit areas (i.e., a set). Thus, a relationship between two sets of translated coordinates can be described according to set language, such as disjoint, intersecting, or subset.

Embodiments of the invention provide systems to optimize the display. Since a display according to embodiments of the invention can be created for utilitarian applications, such as identifying a global distribution of clinical trial facilities, and since elements of the display themselves may include functional information (numbers, text-labels, informative colors, etc.), system embodiments of the invention can render a display having no overlap or superposition of elements. Furthermore, this creates an aesthetically pleasing display, which can encourage people to use an associated service.

System embodiments of the invention can create a display of elements wherein no element is super-positioned over another by pairwise comparing each set of translated coordinates. For each pair of sets, if intersection is detected, the system can transform one or each set of the pair. For example, an area of intersection can be determined, the area of intersection defining an x distance and a y distance. Then, each of the pair of sets of coordinates can be transformed by incrementing the coordinates by ±0.5(x) and ±0.5(y) to move the elements away from the intersection. This generates a new set of coordinates, referred to as transformed coordinates for convenience. A set of transformed coordinates according to embodiments of the invention can have all the same properties as a set of translated coordinates, and system embodiments of the invention can further treat a set of transformed coordinates just as a set of translated coordinates.

Another display optimization provided by system embodiments of the invention is outlier processing. In some embodiments, any group of sets of translated (hereinafter, translated can mean "translated or transformed") coordinates defines a set of display elements. Any set of display elements defines a centroid. Centroid, generally, refers to "the middle of a cluster" and in certain embodiments can be found by determining an intersection of all straight lines that divide the set of elements into two parts of equal moment. In some embodiments, embodiments of the invention provide heuristics for determining a centroid, including, for example, determining an average of all x coordinates and an average of all y coordinates, or a harmonic mean of each. Any method of finding or approximating a centroid is useful in embodiments of the invention.

For any group of translated coordinate sets, one or more of the coordinate sets may be an outlier. Outlier, generally, refers to coordinate set that is numerically distant from the rest of the sets in a group. Specifically, an outlier can be an element that would be drawn on the screen far away from a number of other elements in the same group. To present the elements in a visually useful or pleasing way, system embodiments of the invention can process an outlier so that it is rendered closer to the group in a display than its coordinates would indicate. Outlier processing can involve transforming the coordinates of the outlier (e.g., by reducing a vector magnitude or reducing an x or y value), thereby optimizing the display. In some embodiments, outlier processing can include defining a coordinate field for display with a non-linear scale (e.g., non-linear axes, quasi-log, or similar) so that, for example, a distance of 100 is less than 10 times a distance of 10.

Outlier processing can further involve modifying a visual aspect of a displayed element or a field of display to indicate a true scale of the outlier. For example, the element can be rendered smaller than, or larger than, a proportional rendering would yield (in general, rendering elements according to embodiments of the invention can include rendering their size to correlate with an associated number, for example, of entities at a location). Another modification of a visual aspect of a display included in outlier processing can be rendering a system of grid lines to appear (e.g., behind) one or more elements, the lines being curved or having non-orthogonal intersections, to indicate a "stretching away" in space, thereby indicating that an individual entity is, in-fact, further from a centroid than it otherwise appears. In certain embodiments, outlier processing involves transforming a set of translated (i.e., translated or already transformed) element coordinates to yield a set of transformed coordinates. Optimization of a display can include multiple optimization steps conducted in any order, in parallel, in combination, or simultaneously. For example, elements could be processed to resolve superposition, outliers could be processed, and elements could be re-processed to further resolve superposition. In some embodiments optimization processes— which can include superposition resolution, outlier processing, or other methodologies—are each conducted by an independent routine, module, or object of computer software, each of which can analyze coordinates independently of another. Generally, translation or optimization will yield a set of coordinates corresponding to elements to be displayed.

Figure 25:
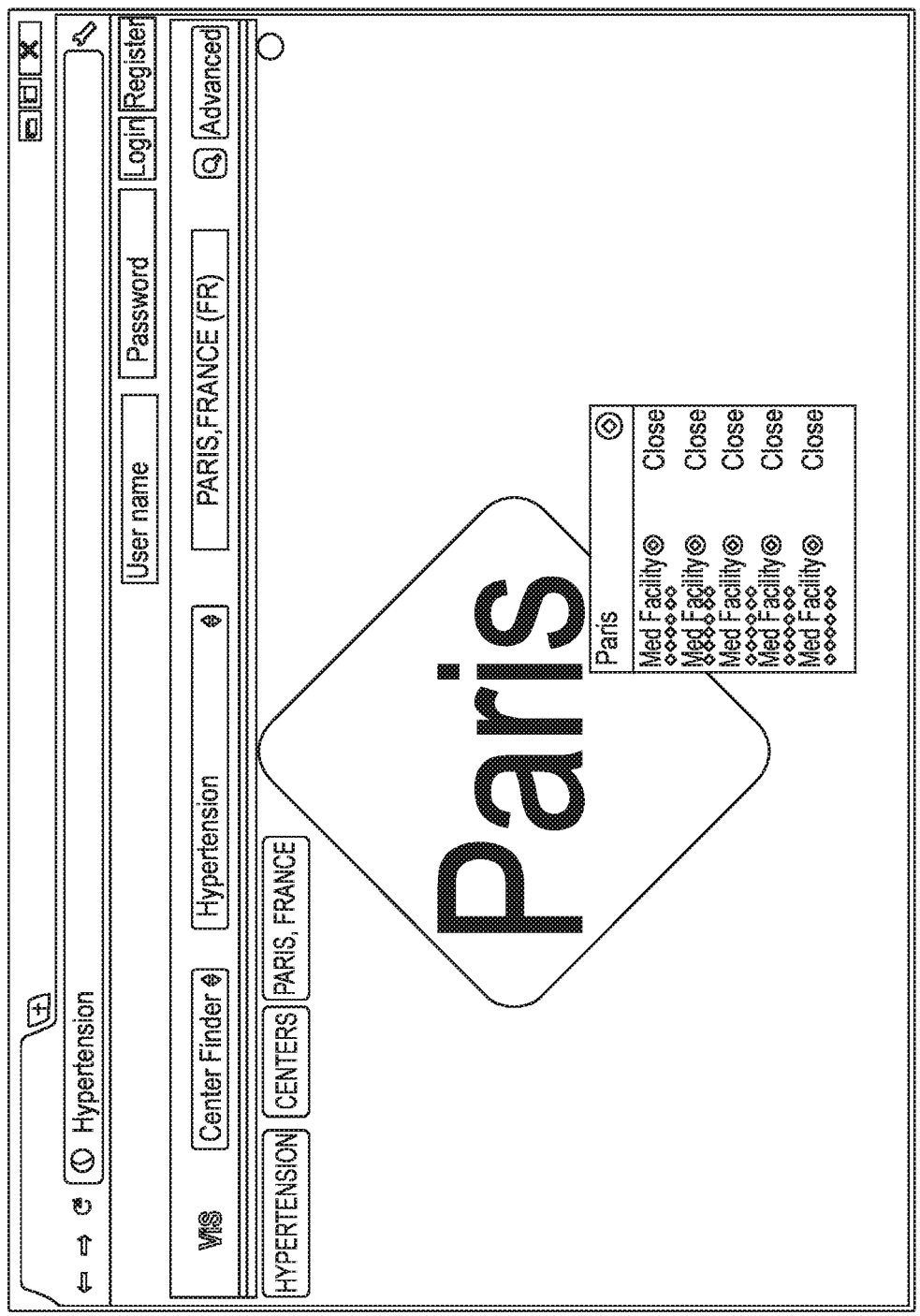
FIG. 25 shows a screen through which to access a center profile.

FIG. 25 shows choosing a location and also shows an element corresponding to a group of hypertension research facilities in Paris, France, according to embodiments of the invention. The positioning, size, and other aspects of the displayed elements can dynamically adjusted, for example, to fit a defined space. A display according to embodiments of the invention can be designed to respond to a user's input. For instance, a display can include map-like elements, and a user can zoom in on certain areas, and systems and methods of embodiments of the invention can re-render or adjust the rendering of the display to include the results of the user's browsing or zooming. Exemplary tools for display are discussed in U.S. Pub. 2011/0270705, U.S. Pub. 2011/0175923, U.S. Pub. 2011/0185286, U.S. Pub. 2010/0106752, and U.S. Pub. 2007/0174331, each of which is hereby incorporated by reference in its entirety.

An element as rendered in a display can optionally contain links, links to links, other elements, and can be interacted with, re-positioned, and influenced by other elements or information. In some embodiments, system and method embodiments of the invention generate output capable of being rendered as a visible display. In certain embodiments, output includes HTML5 elements, which can include, for instance, JavaScript commands or HTML5 elements describing each element. An element can be described to have material displayed within, or associated with, it. In some embodiments, an element is rendered in a display to have keyboard characters or an image in it, and that material can optionally be a link, such as an HTML or HTML5 hyperlink, which can operate to send a web browser to another display. In some embodiments, a link causes a pop-up, such as a pop-up window, a pop-up menu, or a pull-down menu, to appear. An element can include a textual or image (i.e., jpg) label to be displayed when it is selected such that the label contains specific information about the location or active links to profiles of entities conducting business in the corresponding locations. FIG. 2 shows a list of hypertension research facilities in Paris, France, according to embodiments of the invention.

In certain embodiments, a user can set or toggle criteria controlling what is displayed, and system and method embodiments of the invention can respond (e.g., interactively) to show/hide things according to a user's selection of options, criteria, or filters.

A display can be shown so that a user is able to interact with elements (i.e., with the geo-referenced information), for example, through the use of a mouse click or touch on the area of the corresponding polygon. Embodiments of the invention provide display elements capable of being shown or interacted with on a touchscreen or through any other computer monitor.

Embodiments of the present invention provide tools for the display of geo-referenced information on the screen of a computerized system, like a tablet, smartphone, laptop or desktop. The information referenced to each location can be displayed primarily in the form of equilateral convex polygons (e.g. equilateral diamond) that can be, for example, distributed in a HTML5 canvas of adaptable dimensions.

The positions of the polygons can be referenced to the corresponding geo-coordinates of individual locations. Such positions can be dynamically adjusted to fit the space available in the canvas employing mechanisms that detect when a given polygon is superposed with another one, performing corrections though computations of new position combination when that occurs. The sizes of the polygons can be adjusted automatically when necessary to enable the inclusion of all elements inside the electronic canvas. Embodiments of the invention provide a mechanism to detect elements that are far away from the centroid of the visualization and automatically pull them towards mathematically specified positions closer to the other elements.

This web-based visualization system enables the display of multidimensional geo-referenced information by variation of: position of polygons based on latitude and longitude; size of the polygons; color of the polygons; color transparency of the polygons; internal textual label of the polygon; external textual label of the polygon; variations in the width of the line delimiting the polygon; variation in the texture of the filling of the polygon; or any combination thereof. Exemplary tools for display are discussed in U.S. Pub. 2011/0270705, U.S. Pub. 2011/0175923, U.S. Pub. 2011/0185286, U.S. Pub. 2010/0106752, and U.S. Pub. 2007/0174331, each of which is hereby incorporated by reference in its entirety.

A user is able to interact with the geo-referenced information through the use of a mouse click or touch on the area of the corresponding polygon (e.g., touch with mouse pointer or touch with finger on touch screen). Such interaction includes commands to zoom in (into the lower geographic level) or zoom out (to the higher geographic level) from the given geographic location, which can trigger the creation of new visualizations showing the new elements in the chosen geographic level.

An external textual label can appear when the polygon is selected, and can contain specific information about the location, active links to profiles of the entities conducting business in the corresponding locations, or both.

Methods of displaying networks as polygons or similar on-screen icons, based on geo-referenced coordinates associated with the centers or their locations, have been disclosed in the related application U.S. Provisional Patent Application No. 61/569,098, COMPARATIVE EVALUATION AND MARKETING OF RESEARCH ENTITIES, filed on Dec. 9, 2011, the contents of which are hereby incorporated by reference in their entirety.

Dynamic, Disease-Specific Content

Embodiments of the invention display relevant networks based on trial experience, team expertise, patient population, infrastructure, publication record, and degree of global interconnectivity of a research team (not only one person) of participating centers. One concept of embodiments of the invention is that one or more of these factors can be used to develop a center's representation in the display. For example, where a trial planner inputs criteria for centers, they may explicitly use definitions or criteria that limit the inclusion of centers into the display that they see. For example, a trial planner may require that a center has participated in at least one prior clinical trial relating to a disease for inclusion in their present search.

However, in some embodiments, one or a combination of factors is used "behind the scenes" to develop a centers' inclusion in a trial planner's search results. For example, in an attempt to aid a trial planner in discovering the most competent, relevant centers, where a given location is associated with a large number of search results, those search results can be ordered according to an optionally weighted combination of factors. To illustrate, it may be recognized that a prior history of collaborating in multi-site trials is an important indicator of competency to participate in future multi-site trials. Further, it may be recognized that those centers which have recently taken an active role in updating their profile content (as discussed in greater detail below) also tend to be the centers that participate most constructively in present trials. Accordingly, where a trial planner searches a given location for centers to participate in a trial relating to a specific disease, system embodiments of the invention can recover all N centers in that location with competencies relevant to that disease, and can present them order 1, 2, . . . , N according to a combination of the number of multi-site trials in which the center has participated and the time since the center has last updated its profile, each optionally multiplied by a weighting factor.

Preferably, a database of embodiments of the invention includes many research centers (e.g., more than 100 and preferably more than 1,000). In some embodiments, thousands of different research centers are included, distributed across many nations, jurisdictions, or geographical regions (e.g., dozens or more than one hundred different nations may be included).

Moreover, due to the ability of centers to update their profiles with ease, a center profile can be offered that is current, to the hour and minute. Where prior art paper-based methods required days, weeks, or longer for information to travel from trial planner to center (in the form of feasibility questionnaire) and back, and would only include that information which either party thought to include at the relevant time, embodiments of the present invention provide a profile based on contents that includes all information gathered or input by centers. The profile can be as current as the last edit. Further, some embodiments of the invention provide tools to update the trial planner as relevant information changes. For example, a trial planner may require only centers with helicopter landing facilities and a working MRI. A center that had appeared in a trial planner's pre-qualified list may update its profile to indicate that its MM system is out of service, and the trial planner's list can be updated to reflect that fact. In some embodiments, a notification can be sent to the trial planner. In similar fashion, if a center that otherwise qualifies and has an MRI facility, but no helipad, completes construction of a helipad and so updates their profile, that center can be added to the trial planner's list.

By such means, a trial planner can analyze and evaluate a global network of clinical research centers according to general and disease-specific parameters updated as medicine's state-of-the-art and commonly used trial protocols (or comparative treatments) evolve.

Aspects of information about research centers include information relating to: regulatory environments; candidate patient populations; and clinical capacities as well as trial-specific center and investigator competencies. For example, center profiles may contain information relating to the availability of a regulatory fast track in the controlling jurisdiction, or estimates on times typically involved in obtaining regulatory approval such as, for example, acceptance by a local agency that proposed trials meet with local good clinical practice (GCP) requirements.

Before turning to center and investigator trial competencies, disease specific capacities of centers are discussed. While a number of specific exemplary capacities, organized by disease, are listed herein below, that listing is not limiting. Rather it illustrates an exemplary embodiment. Centers may provide information about particular hardware, lab equipment, medicines, or other infrastructure that they possess as it relates to a disease. Any single item can be cross-listed under more than one disease in some embodiments (e.g., x-ray machine can be listed under broken bone treatment, dental, and lung disease). A disease can be included in a center profile having no items listed under it (e.g., where a center intends to indicate an availability to participate in a type of trial without having any specialized equipment). In some embodiments, centers or individuals can propose new, or not yet listed, diseases or conditions for inclusion in the database going forward. In certain embodiments, profiles include one or more specific clinical capacities that are shown within a user-selected category that may be selected from adult cognitive disorder; Alzheimer's; arrhythmia; breast cancer; cerebrovascular disorder; CNS infection; diabetes; dyslipidemia; hematologic cancer; HIV infection; hypertension; influenza; ischemic heart disease; lung cancer; mood disorder; pneumonia; prostate cancer; schizophrenia; viral hepatitis; another disease; or any combination thereof.

In certain embodiments, capacities of the centers are organized according to the local availability of drugs or treatments used as comparators in clinical trials of specific diseases. For example, a global trial might need to use a certain type of β-lactam antibiotic or selective-serotonin reuptake inhibitor for comparisons with the drug to be tested. That drug needs to be commercially available locally so that it can be used as a comparator treatment. Considering that a given drug might be available in some countries but not in others, it is important to be able to search for the centers that happen to operate in locations where the comparator drug planned for the trial is available.

In certain aspects, information about centers includes anonymized information about available patient populations. One aspect of the invention is that patient information is aggregated statistical and demographic information, and does not include any information identifying individual patients. Thus a trial planner can query for centers that have historical or present access to patient populations that will satisfy the planner's proposed study. By not including information identifying individual patients, a tool of much greater general availability is offered in that participants can use system and method embodiments of the invention without invoking strict patient confidentiality laws such as provisions of the Health Insurance Portability and Accountability Act in the United States or similar provisions in other jurisdictions, thereby providing good access to a tool of general value and applicability to the work of trial planners. Searching centers by patient population is discussed in the related application U.S. Provisional Patent Application No. 61/569,098, COMPARATIVE EVALUATION AND MARKETING OF RESEARCH ENTITIES, filed on Dec. 9, 2011, the contents of which are hereby incorporated by reference in their entirety.

Group Composition

In some aspects, embodiments of the invention generally relate to a system for composing a group of assets. System embodiments of the invention provide an interface for querying general information and disease-specific information pertinent to location, site, and investigator competencies as demonstrated through factors such as past or ongoing clinical trials, publications, collaborations, and networks.

Embodiments of the invention generally include an API for accessing data about assets and receiving one or more criteria input by a user (as described above). Systems and methods embodiments of the invention can determine that information items at extrinsic sources satisfy the criteria (as discussed above), thereby identifying a set of assets satisfying the user's search criteria. In some embodiments, the resulting set will include a subset of all research entities in a local database, an external database, or both. For example, if the database included three research entities, systems and methods embodiments of the invention could identify a set of two research entities that matched certain criteria. In general, embodiments of the invention provide the ability to identify a commercially or scientifically relevant set of assets, such as a set that is optimized to perform a clinical research project.

Once a set of assets is identified, the identities of those assets are streamed to a user. That set of assets may optionally be written into a file (a file can be a set of related files, such as a first file that identifies the file names and paths of a number of other specific files). A file can be a digital file, for example, stored on a hard drive, SSD, CD, or other tangible storage medium. A file can have an existence as an attachment in someone's email (i.e., existing as IPv4 packets or IPv6 packets or similar) or as an internet transmission (e.g., as packets being sent from a server to a client, for example, through a Network Interface Card, modem, wireless card, or similar, on the server), although a file according to embodiments of the invention is capable of being written to tangible storage medium.

Writing a file according to embodiments of the invention involves transforming a tangible, non-transitory computer-readable medium, for example, by adding, removing, or rearranging particles (e.g., with a net charge or dipole moment) into patterns of magnetization by read/write heads, the patterns then representing new collocations of information desired by, and useful to, the user. In some embodiments, writing involves a physical transformation of material in tangible, non-transitory computer readable media with certain optical properties so that optical read/write devices can then read the new and useful collocation of information (e.g., burning a CD-ROM). In some embodiments, writing a file includes using flash memory such as NAND flash memory and storing information in an array of memory cells made from floating-gate transistors.

In some embodiments, a user interacts with a visual interface and puts in criteria, which are received by embodiments of the invention and used to generate a list of assets. The list is sent to a web browser, file, or app on the user's device, for instance as HTML5, where it is rendered into a visible display. The user then interacts with the list, resulting in the set of research entities being written to file. User interactions that cause the set to be written to a file include clicking a button ("order now"), or right-clicking and choosing a command (download . . . ), or confirming through a dialog box an intention to save the list. Systems and methods embodiments of the invention can thereby write a file comprising a group comprising the identity of the first research entity and the identity of the second the research entity.

Systems and methods embodiments of the invention provide forms of output for making the set of assets available to a user.

One form of output includes an interactive visualization tool (described in U.S. Pub. 2013/0151275, incorporated by reference) that dynamically shows the number of assets matching the chosen criteria by global location though sizes of geo-referenced convex geometric forms, such as equilateral diamonds, in an electronic canvas.

Another form of output includes lists of assets, which can be segregated by their respective locations. The lists of centers can be clickable links that lead to the respective profiles of research centers containing information about their intrinsic capabilities.

In one format, where the output can be a group of research entities, embodiments of the invention provide a dynamic, interactive display of one or more elements. Each element can indicate a number of research entities matching the user's criteria and a location indicated by the position of that element. The number of research entities can be indicated for example, by the size of the element. The elements can be a convex polygon such as an equilateral diamond. Each element corresponds to a local sub-group of the group of research entities. Each element can further display, or interaction with the element can lead to the display of, a list including the local sub-group of research entities.

In a second format, embodiments of the invention provide output in the format of a group of research entities (e.g., as a list), segregated into sub-groups (e.g., shorter lists) by the locations of the entities.

In some embodiments, the generation of the output can be controlled by the interposition of an e-commerce interface that releases the information upon acceptance of an acceptable form of payment, including charging to pre-registered credit cards, charge accounts or subscriptions. Users from the same institution may have shared accounts (such as corporate accounts) under which the output generated can be saved and center profiles of interest can be bookmarked for posterior viewing. Exemplary methods for processing payments are discussed in U.S. Pat. Nos. 7,356,502, 7,542,943, 7,818,251, U.S. Pub. 2004/0210521, U.S. Pub. 2002/0032648, U.S. Pub. 2005/0192901, U.S. Pub. 2010/0100467, each of which is herein incorporated by reference in its entirety.

By accessing information about clinical trial assets from suitable sources, competencies of the assets can be shown for evaluation by showing a center's real and relevant experience. Including such information further provides valuable tools for sorting and ordering search results. Suitable sources for the data include services and databases such as Medidata's. In certain embodiments, past or present clinical trials are stored or tracked in a database accessed by systems and methods embodiments of the invention. The participation of individual centers in these trials is tracked in association with the trials. Information about clinical trials can be obtained, for example, from online databases of clinical trials. See, e.g., Ross, et al., Trial publication after registration in clinicaltrials.gov: a cross-sectional analysis, PLoS Med 6(9):e1000144 (2009).

Databases accessed by or created and stored by system and method embodiments of the invention can include information about past trials, ongoing trials, planned trials, or a combination thereof. By including information about clinical trials, databases of embodiments of the invention can include information about research centers that participate in those trials. By including information about research centers that participate in given trials, embodiments of the invention include tools for identifying centers that have collaborated in clinical trials (here, optionally meaning centers that have at least both participated in one clinical trial). Further, by including trials in databases of embodiments of the invention, the databases can include information identifying investigators who have participated in those trials. This provides, for example, one possible source of information by which system and method embodiments of the invention can automatically provide sets of assets. As discussed herein, above, and in U.S. Provisional Patent Application No. 61/569,098, COMPARATIVE EVALUATION AND MARKETING OF RESEARCH ENTITIES, filed on Dec. 9, 2011, the contents of which are hereby incorporated by reference in their entirety, embodiments of the invention provide valuable tools for the clinical trial planner to use in planning a clinical trial. The tool includes an API for gathering information pertaining to clinical research assets.

In some embodiments, the importance of a trials database lies in how the information is used in sorting and presenting the results of a trial planner's database queries. As discussed above, participation in recent clinical trials can be used to weight the relative position of a center on a list of results.

Certain aspects of the invention include a database of investigators. System and method embodiments of the invention can use information obtained from a database of clinical trials to pre-populate, or contribute to, a database of investigators. Investigators themselves may "log in" and edit, contribute to, or update their profiles. Investigator profiles provide a valuable tool by which trial planners can evaluate centers for inclusion in a trial. For example, the availability of a highly qualified investigator at a given center can indicate the potential value of that center for inclusion. That is, the roster of investigators associated with a center can be used as an indicator of a competency of that center. A trial planner can view the profile of any investigator, including previous trials the investigator has participated in as well as publications of that investigator and other centers where that investigator has worked.

Certain aspects of the invention provide systems and methods for showing a publication history of an investigator associated with a center. In particular, embodiments of the invention provide for disease-specific viewing of publication histories, in which those publication histories can be collected automatically or provided through the efforts of investigators or center personnel. Publication lists can be provided as a tool for a trial planner to ascertain the relevant experience of a center or investigator. Publications can also aid in automatically identifying historical collaborations among investigators, thereby being used within system and method embodiments of the invention in building networks.

Certain aspects of the invention provide networks that include investigators or centers and relationships among them. A network can be a set of relationships explicitly disclosed, for example, through an investigator or center's profile. A network can also be used "behind the scenes" by tools of embodiments of the invention to leverage relationships among participants to provide information to trial planners identifying centers or investigators relevant to a prospective clinical trial. Use of a network feature according to embodiments of the invention allows trial planners to easily see centers that are connected and that share similar features or operating protocols, which can aid the trial planner in further identifying more potential centers for inclusion in a study.

Some embodiments of the invention provide tools for clinical research center marketing through the capture of general and disease-specific analytics that can be automatically updated as medicine's state-of-the-art and commonly used trial protocols (or comparative treatments) evolve. System embodiments of the invention can be operated to collect or stream information from research center personnel as well as other sources. This allows data to be structured according to questions about general as well as disease-specific capabilities of an asset such as a research center, geographic location, or primary investigator. In certain dimensions, questions can be about extrinsic and intrinsic aspects of a center. In another dimension, data can be factual historical data about clinical trials the research center has participated in or prospective information about clinical trials the centers markets itself as available for.

To update general and disease-specific information in a center profile, research center personnel can access the embodiments of the invention and identify the center they represent.

FIG. 25 shows a screen through which a research center representative could browse to the location of their center and see a list allowing them to click on a link to claim their center. Claiming a center to edit the profile can require authenticating yourself to the system. This can involve, for example, creating a login and password, verifying their official affiliation with the center, or responding to an invite to join the system. Upon claiming their center, personnel can be given the opportunity to edit or update the center profile.

FIG. 26 shows a part of a center profile according to certain embodiments, including the availability of the "Edit Profile" link near the top-right of the screen. This allows a representative from a center to access the system and affirmatively update that center's information as represented within the system.

In certain embodiments, system and method embodiments of the invention provide information about available patient populations, both in general and for specific diseases, by asset. In preferred embodiments, patients are anonymous and aggregate, statistical, or demographic data is solicited and received in system embodiments of the invention. Patient data can include, in total or for any disease, a number of patients as well as any other population characteristics such as age structure (e.g., in the sense of an age structure pyramid or actuarial life table) with axes optionally for gender, ethnicity, health or other factors (e.g., education, income, residency, etc.). Patient data can include information about sets of patients that have previously participated in studies, that are presently participating or that are prospectively able to participate. Patient data can include historical recruitment returns as well as any other data relevant to recruiting patients into clinical trials. In all cases, patient data is preferably accessible in total and per disease. Accordingly, embodiments of the invention provide a tool for the marketing of a center's prospective ability to recruit patients into a clinical trial in a disease-specific manner.

One marketing tool valuable for clinical research centers is the competencies of center personnel and investigators. Editing a center profile can include providing information about those personnel or editing or updating such information. In some embodiments, a center profile includes data sets capable of being displayed on web pages to show personnel or investigators associated with a center. Those personnel affiliations can be shown in total or in a disease-specific fashion. For example, Dr. Jo may work at Alpha Center and be a specialist in hepatitis. Dr. Terry may work at Alpha Center, specializing in CNS diseases. A center can market itself using system embodiments of the invention by editing its center profile to include Drs. Jo and Terry in a list of the total center's personnel affiliations. However, the center can further edit its profile so that when a trial planner sorts by disease, the profile will list only Dr. Jo under hepatitis and only Dr. Terry under CNS disease.

Certain embodiments of the invention include tools such as a web API to identify center personnel and stream that information in response to a planner's query so that representative of the center need not fill out a profile. In fact, in some embodiments, streaming the asset data plays an operative role in driving the successful promotion of the trial planning tools disclosed herein. It is contemplated that clinical trial investigators and other medical professionals may be attracted to scrutinize a data upon discovery of the fact that they are themselves already viewable through the system. This information can be automatically displayed publically, or kept private, pending verification by the appropriate individual (to whom an email can be transmitted upon the automatic pre-population step using, for instance, an email address as scanned from the text of a publication from which the personnel's affiliation with the institution is also scanned). A medical professional may be interested to see that they are shown as affiliated with a clinical research center that is being promoted as prospectively available to conduct clinical trials. That professional may review the listing and create a log in to confirm or edit their listed affiliation with the center. Moreover, historical collaborations can be presented to the professional, who can be prompted to verify or edit the listing of historical collaborations.

A history of clinical collaborations can be retrieved from publically accessible databases of clinical trials for from scanning appropriate document listings in online libraries (e.g., PubMed). Publication references can be retrieved and listed as found, or regular expression can be used to extract author names, article titles, journal names, vol: first page-last page, and year. From this data, presumptive collaborations among joint authors can be identified (i.e., jointly listed authors on a clinical trial publication can be presumed to have co-collaborated on the study), and those professionals can be listed in their respective profiles as having collaborated with one another, in total or in a disease specific matter.

It will be appreciated that the information about assets that is streamed to a trial planner, such as what information is featured most prominently, may evolve as industry best practices develop. For criteria that may be important to trial planners generally, see Warden, et al., Rationale and methods for site selection for a trial using a novel intervention to treat stimulant abuse, Contemp Clin Trials 33(1):29-37 (2012); Potter, et al., Site selection in community-based clinical trials for substance use disorders: strategies for effective site selection, Am J Drug Alcohol Abuse 37(5): 400-7 (2011); Taylor, et al., Optimizing stroke clinical trial design: estimating the proportion of eligible patients, Stroke 41(10)2236-8 (2010); and Maggon, Investigator and site selection and performing GCP clinical studies in India, Control Clin Trials 25(4):366-77 (2004), the contents of which are incorporated by reference herein in their entirety for all purposes. Further discussion may be found in Demeter J. Selecting sites and investigators. An approach for Central and Eastern Europe. Appl Clin Trials 11(3):56-66 (2002); Bleyer W A. The U.S. pediatric cancer clinical trials programmes: international implications and the way forward. Eur J Cancer 33(9):1439-47 (1997); Topol E. J., et al., For the Virtual Coordinating Center for Global Collaborative Cardiovascular Research (VIGOUR) Group. Perspectives on large-scale cardiovascular clinical trials for the new millennium, Circulation 95(4):1072-82 (1997); Mahony L, et al., Pediatric Heart Network Investigators. The pediatric heart network: a primer for the conduct of multicenter studies in children with congenital and acquired heart disease. Pediatr Cardiol 27(2):191-8 (2006); Atkinson, Using the Internet to search for cancer clinical trials: a comparative audit of clinical trial search tools, Contemp Clin Trials 29(4):555-564 (2008), the contents of which are incorporated by reference herein in their entirety for all purposes.

Further, additionally and alternatively, system embodiments of the invention can automatically retrieve answers for a trial planner's questions using database search and query functions as programmed according to programming methodologies known in the art in languages or development environments discussed in greater detail below.

By using the automated tools to access information retrieved from databases of clinical trials, databases of publications, from the input of other persons whom have collaborated with more than one center, sets of assets can be pre-qualified by matching search criteria provided by the planner. Accordingly, embodiments of the invention provide tools that make the accessing of technical information quick and efficient, by streaming information identified to be pertinent.

Further, while information is organized into sets by disease, information can be automatically populated across sets where applicable. For example, where a person edits a profile under the heading of "osteoporosis" to indicate that they have an x-ray machine, under the heading of "trauma treatment", the availability of an x-ray machine can be affirmatively listed. In some embodiments, where an investigator in one center indicates that that center has certain equipment and that that center often collaborates with a second center, the availability of that piece of equipment under the second center can be automatically pre-populated as "can be arranged". Further, general questions can be scripted and presented by a computer program before the disease-specific questions are asked and where certain categories of information are of general as well as disease-specific importance (e.g., helipad may appear under general information as well as under trauma treatment; x-ray may appear under general information as well as osteoporosis), those questions can be asked once as general questions and used to populate the disease-specific profiles. Thus, embodiments of the invention provide integration of general questions with disease-specific questions so that the center representatives do not have to repeat the general information for each disease-specific profile.

It will appreciate that system and method embodiments of the invention allow for quick updating of infrastructure information, allowing centers to share them with interested trial planners in a time-efficient manner. For example, if certain jurisdiction certify medical sites contingent on certain inspection outcomes, each annual inspection can promptly be recorded in the center profile. In fact, in some embodiments, future prospective events (such as governmental inspections) are indicated in a profile so that trial planners can be aware of upcoming significant events.

Using system and method embodiments of the invention to market their clinical trial capacity, as well as to promote the competencies and qualifications of their personnel and their history and activity in clinical trials, centers can establish and control relationships with other stakeholders such as other centers, trial planners, investigators, sponsors, and government personnel, for example.

Networking Tool

Certain aspects of embodiments of the invention provide tools by which planners can search across networks, or digital representations of connectivity among assets as relates to capacity to participate in clinical trial. Assets, or nodes, in networks can be individual investigators, research centers, other entities (e.g., academic institutions), or a combination thereof.

Figure 27:
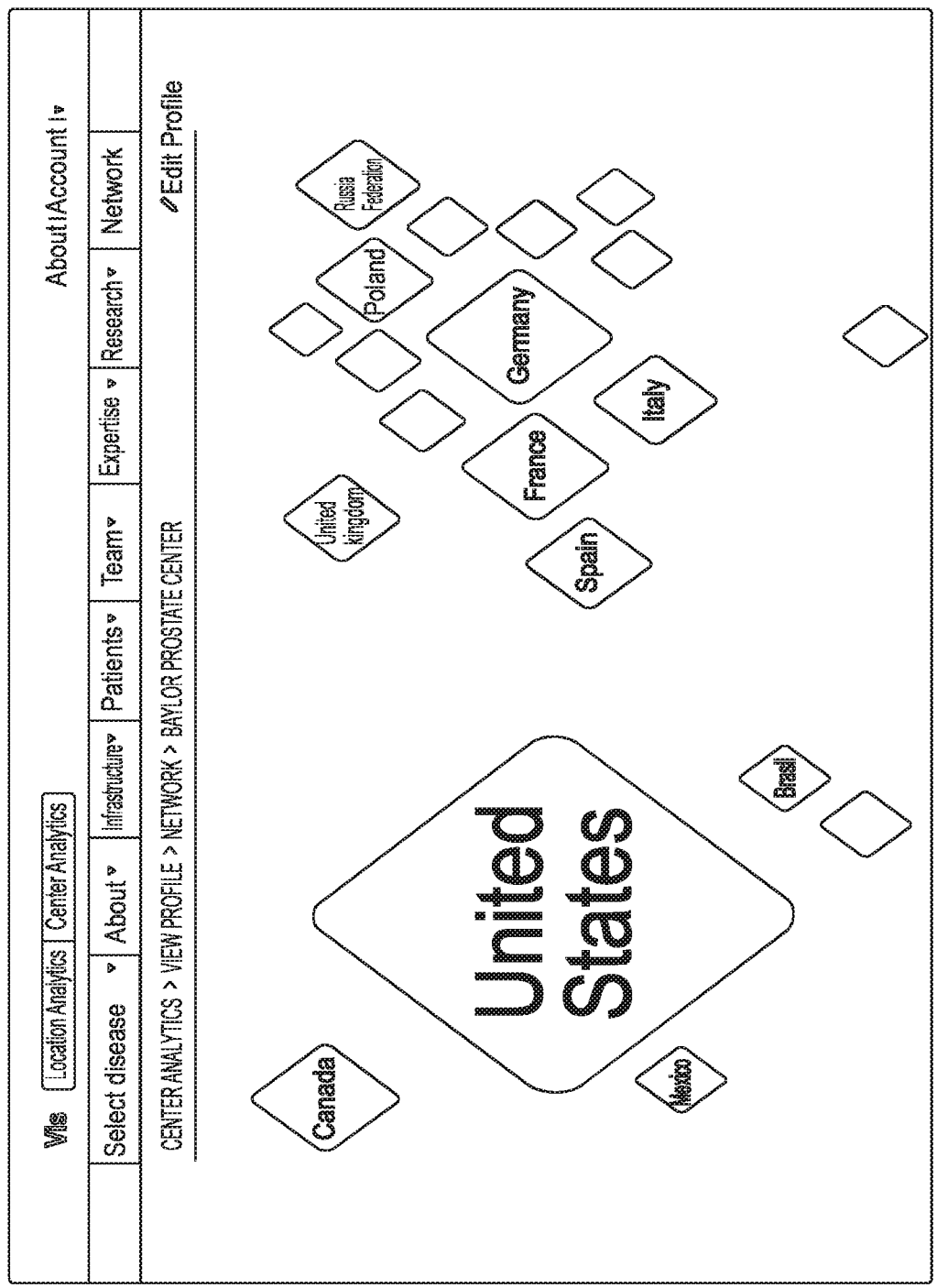
FIG. 27 shows a home screen for viewing a network.

FIG. 27 shows a home screen for viewing a network. Here, the network of the Baylor Prostate Center is illustrated. From this display, one may see that Baylor Prostate Center has, in its network, entities in Canada, United States, Mexico, Brazil, United Kingdom, Spain, France, etc. Those entities may include other research centers or personnel. In general, a network may refer to connections defined by past collaborations, institutional affiliations, potential or intended collaborations, or collegial affiliations. Certain embodiments of the invention provide systems and methods for building and populating networks. Tools for network building include automatic, internet-searched based tools as described elsewhere herein, as well as user-interface tools by which personnel can update and edit their network connections.

FIG. 28 shows an exemplary screen by which a representative of Baylor Prostate Center may edit their network. As shown in FIG. 28, the system is displaying four institutions with which the entity has established network connections (e.g., Massachusetts General Hospital, Park Hospital, Longhua Hospital, and Hospital das Clinicas). Furthermore, the system is displaying institutions and individuals that have been discovered and pre-populated as candidates or further inclusion in the network. Here, for example, the system has suggested that a Dr. Fadem may have a history of 10 collaborations with personnel from the Baylor Prostate Center. To further develop the network personnel from the Baylor Prostate Center may wish to invite Dr. Fadem to join the network.

Figure 29:
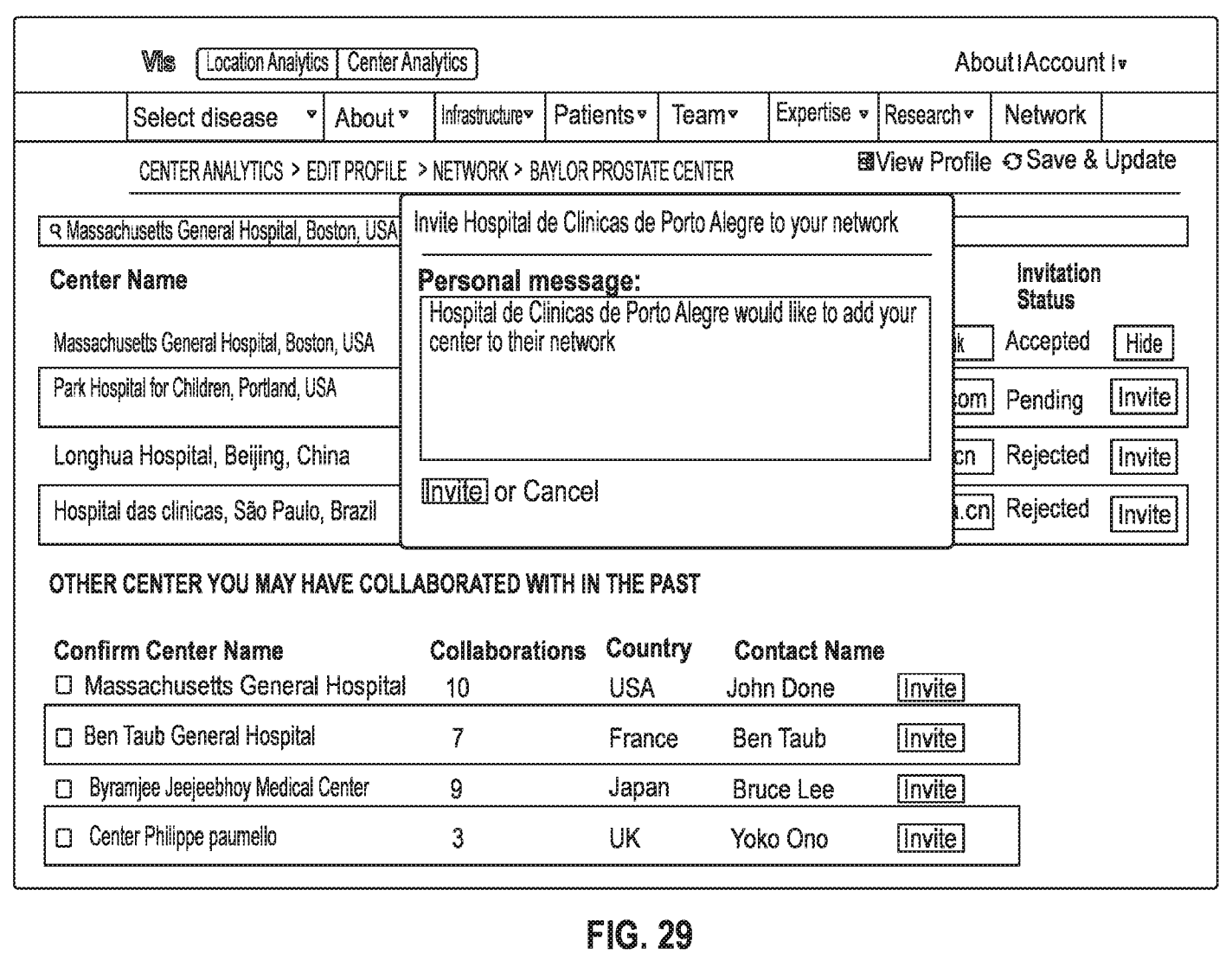

FIG. 29 shows a screen for inviting an entity to join a network. Networks can include nodes and connections. A node is generally a representation of an entity, and may include affiliated entities (although an affiliation with an entity can be a connection). Entities can be any entity, such as centers, investigators, sponsors, etc. Connections can be historical collaborations, other collaborations, institutional affiliations, co-authorship, etc. Use of networks provides a tool for centers to market themselves by demonstrating to trial planners the inherent capacity to participate in multisite clinical trials. Use of network further provides a mechanism to drive participation in system embodiments of the invention. It is contemplated that upon receipt of a network invitation, individuals will be motivated to accept and join the network, for example, to promote their own institutional and professional accomplishments and capacity.

System and method embodiments of the invention can render a profile for an asset (e.g., an investigator profile, a site profile, or a location profile).

In some aspects, embodiments of the invention provide a system for rendering a profile for an asset. An asset may be an investigator, a geographic location, or a research entity. Profiles of locations are discussed in U.S. Pub. 2013/0151279, incorporated by reference. System and method embodiments of the invention obtain information about an asset, normalize the information, and use it in a profile, optionally storing the normalize data in a local database of the system. For example, a database can include a file on a computer into which information is input. In some embodiments, a database is provided by an outside vendor. Databases and profiles are described in U.S. Publ. 2003/0191664, U.S. Pat. No. 7,054,823, U.S. Pub. 2002/0023083, U.S. Pub. 2009/0089392, U.S. Pat. No. 7,647,240, U.S. Pub. 2010/0211411, U.S. Pub. 2003/0108938, U.S. Pub. 2006/0287997, and U.S. Pub. 2004/0078216, each of which is herein incorporated by reference in its entirety.

Information can be prepared for access by rendering a profile. Embodiments of the invention provide methods for rendering a profile for an asset. Certain embodiments of the invention provide a disease-specific profile for a research entity. Thus, a lab can have, for example, an impetigo profile and a breast cancer profile. In some embodiments, a lab or center will have profiles that are very specific for categories of disease or more general. Thus, there could be a profile for Johns Hopkins Cancer and Johns Hopkins Allergies, or there could be profiles for Sidney Kimmel Teratoid/Rhabdoid Tumor and Sidney Kimmel Merkel Cell Carcinoma. A profile generally includes a collection of information related to a clinical research facility and optionally its activity relating to a disease.

System and method embodiments of the invention compose or render profiles, which can include information from an internal database, a first external source, a second external source, or any combination thereof. Composing can include the steps of reading (e.g., by a processor) information from a source, processing or normalizing the information according to instructions, and creating output (e.g., XML, HTML5, HTML, text, an image such as a jpeg, ping, or tiff, or any other output) capable of being displayed or rendered. This output can be written to a file. In certain embodiments, composition includes choosing, e.g., based on criteria (i.e., user-supplied criteria, criteria that result from a calculation or logical operation, externally obtained), information to occupy or define fields of a profile. Such fields could be fields for title, name of entity, disease, location, facility size, number of previous studies, availability, availability of patients for particular study type, peer-review setting, notes, or any other information item. Rendering generally refers to the process of showing a composition so that a human could perceive it. For example, a web browser's (i.e., Internet Explorer, Dolphin Browser HD v. 7.2.0, Google Chrome, etc.) display of HTML, HTML5, XML according to a cascading style sheet (CSS), Flash animation, Java animation or display, or other file (e.g., text file) generally is a rendering. A composition generally includes one or more information items, as retrieved from a database or the internet, or as calculated or processed by a processor based on inputs from a database or the internet. In a preferred embodiment, system and method embodiments of the invention use a tool such as a web API to access two or more sets of data about clinical trial resources from external sources, match a portion of the data to a query by a trial planner relating to a prospective clinical trial, and tailor the portion of the data to create shareable information describing an asset qualified for the prospective clinical trial. Tailoring can include normalizing. After processing two or more information items in this fashion, a composition is produced including a list of assets and optionally a profile for each asset. Some embodiments of the invention provide intrinsic and extrinsic information about an asset. Generally, extrinsic aspects of a research center or facility are location specific. Extrinsic properties include, for example, research infrastructure, research activity, patient population, research personnel, cost, and regulatory environment. Embodiments of the invention can also include the intrinsic properties of the research centers, including both general and disease-specific information about infrastructure, patients, research support personnel, investigators, publications, recruitment performance in clinical trials, and global collaborators. The database optionally includes metrics on historical cost-per-patient for recruitment at each research center, average time-span to recruit a full patient load, or realization rate of recruitment efforts by research centers. Accordingly, a trial planner can include as a search criterion a desired value for one of these metrics.

Embodiments of the invention provide an interactive online clinical research intelligence platform, which enables clinical trial planners to interactively find assets and evaluate their intrinsic and extrinsic disease-specific characteristics. System and method embodiments of the invention enable the trial planner to select a disease or location of interest through interaction with dynamic geo-referenced convex geometric forms distributed on the screen of a computer, tablet or smartphone. The trial planner can evaluate extrinsic characteristics of the assets by evaluation of clinical research-related comparative metrics concerning the locations in which the assets such as research centers operate (including neighborhood, city, state, country, and region). More specifically, the extrinsic metrics are related to local: research infrastructure; research activity; patient population; research personnel; cost; and regulatory environment.

Certain system and method embodiments of the invention integrate with information systems or enterprise resource planning systems or marketing software to feed into those systems aggregate data about patient contacts, potential clinical trial contacts, or other data.

As will be appreciated from the discussion herein, system and method embodiments of the invention may be implemented through the use of computer hardware and software. Implementations of systems for clinical trials are discussed, for example, in U.S. Pat. No. 7,711,580; U.S. Pub. 2006/0178906; and U.S. Pub. 2009/0292554, the contents of each of which are incorporated by reference herein in their entirety for all purposes.

System embodiments of the invention can include one or more computer devices.

Figure 30:
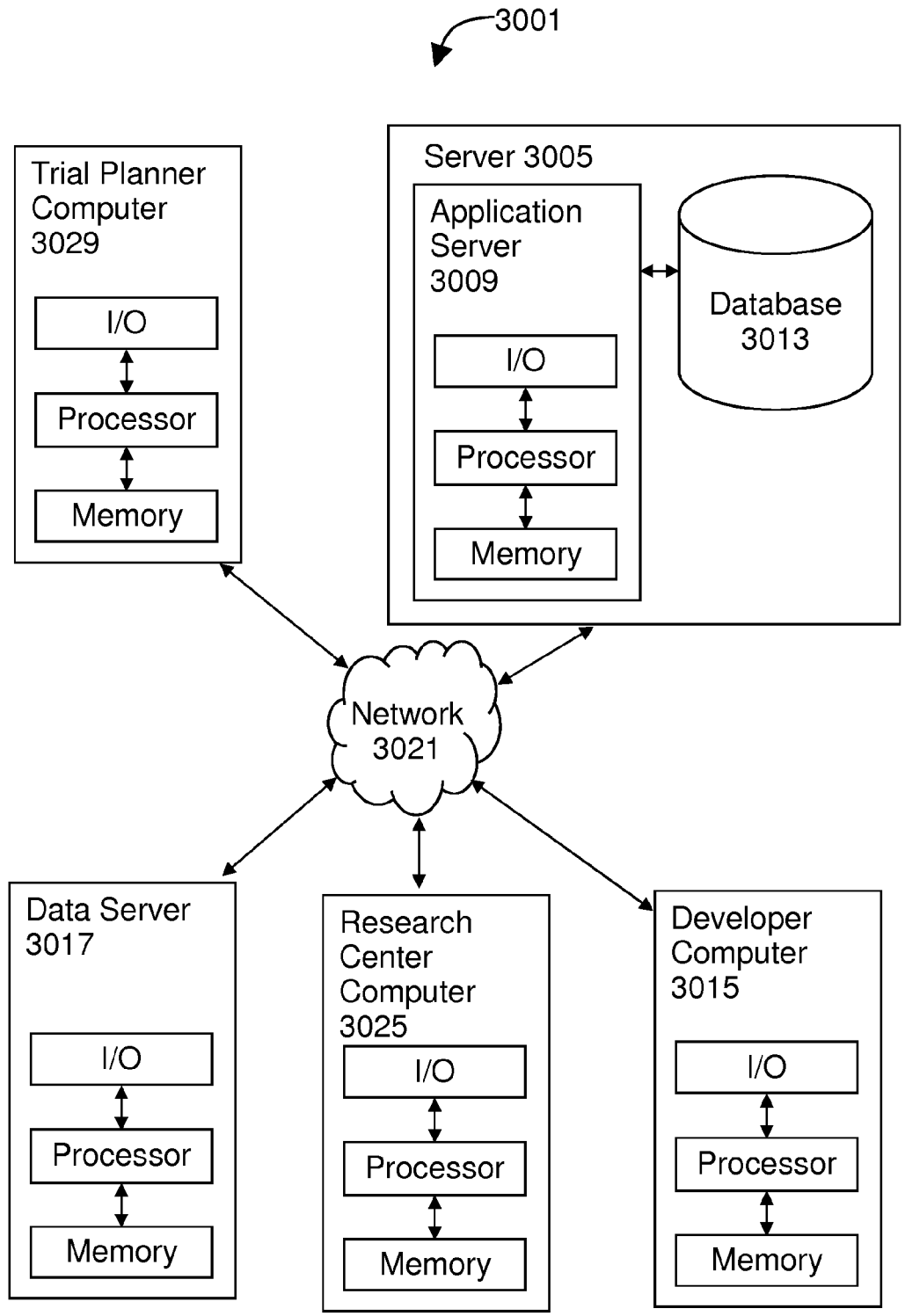
FIG. 30 shows an exemplary computer system according to certain embodiments.

FIG. 30 shows an exemplary computer system 3001 according to certain embodiments. Some embodiments of the invention provide a system 3001 including a server 3005 that can include application server 3009 and database 3013, either as a single computer device or a combination of multiple computer devices. In general, a computer device is an apparatus with an input/output (I/O) mechanism coupled to a processor that is coupled to a tangible, non-transitory memory.

System 3001 generally includes one or more computers including, for example, any of server 3005, developer computer 3015, trial planner computer 3029, research center computer 3025, and a data server 3017, and computer of system 3001 may generally communicate by sharing data with one another over network 3021. In some embodiments, server 3005 includes application server 3009 configured to collect or receive information relevant to one or more of a research center, investigator, publication, clinical trial, disease, medication, medical hardware component, or similar, or combination thereof. Some embodiments of the invention include database 3013, for example, stored in the memory of server 3005 or as a separate hardware component with its own computer hardware, for example, accessible by application server 3009.

The communications between server 3005, developer computer 3015, trial planner computer 3029, research center computer 3025, a data server 3017, and computer of system 3001 may communicate over network 3021 in whole or in part by use of encrypted communications.

Server 3005 can be configured to receive, through its input I/O device, input over network 3021. As discussed above, client input can include a criterion for a search or an interaction with a display. Client input can also include a login (i.e., username) or password.

As one skilled in the art would recognize as necessary or best-suited for performance of the method embodiments of the invention, trial planner computer 3029, research center computer 3025, or data server 3017 are computers. In a preferred embodiment, they can each be one of: laptop, desktop, or handheld computing devices such as smartphones, iPhones, tablet computer, laptops, PDAs, computers, or e-readers. In some embodiments, server 3005 can include hardware such as a Hitachi Compute Blade 500 computer device sold by Hitachi Data Systems (Santa Clara, CA). A processor in a computer device can be, for example, an E5-2600 processor sold under the trademark Xeon by Intel Corporation (Santa Clara, CA). A computer generally includes a memory coupled to a processor and one or more input/output (I/O) device.

A processor may be provided by one or more processors including, for example, one or more of a single core or multi-core processor (e.g., AMD Phenom II X2, Intel Core Duo, AMD Phenom II X4, Intel Core i5, Intel Core i& Extreme Edition 980X, or Intel Xeon E7-2820). In certain embodiments, a computer may be a notebook or desktop computer sold by Apple (Cupertino, CA) or a desktop, laptop, or similar PC-compatible computer such as a Dell Latitude E6520 PC laptop available from Dell Inc. (Round Rock, TX). Such a computer will typically include a suitable operating system such as, for example, Windows 7, Windows 8, Windows XP, all from Microsoft (Redmond, WA), OS X from Apple (Cupertino, CA), or Ubuntu Linux from Canonical Group Limited (London, UK). In some embodiments, any of consumer computer 201, provider computer 281, production computer 261 may be a tablet or smartphone form factor device and processor 281 can be provided by, for example, an ARM-based system-on-a-chip (SoC) processor such as the 1.2 GHz dual-core Exynos SoC processor from Samsung Electronics, (Samsung Town, Seoul, South Korea). Some embodiments of the invention include a specialized device with processing or memory capabilities such as firmware, an application-specific integrated circuit (ASIC), or a field programmable gate array (FPGA). In general, firmware refers to a combination of persistent memory with program code and data stored in it. In general, an ASIC or an FPGA is an integrated circuit configured after manufacturing to operate as a device to implement methodologies of embodiments of the invention. In some embodiments, a custom form-factor device or a device of embodiments of the invention having a form factor other than a familiar laptop, tablet, or desktop computer form factor will include one or more of firmware, an ASIC, or an FPGA, and may further include I/O devices such as one or more of a monitor, button, switch, Ethernet port, Wi-Fi card, touchscreen, USB port, infrared device, or similar, or a combination thereof.

Computer memory generally refers to a machine-readable medium and may generally be present in the form of random access memory (RAM), read-only memory (ROM), or a combination thereof. Memory preferably includes a tangible, non-transitory computer-readable storage medium. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); magneto-optical disks; and optical disks (e.g., CD and DVD disks). While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions.

Input-output devices generally includes one or a combination of a video display unit or monitor (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem, monitor, keyboard, mouse, data jack (e.g., Ethernet port, modem jack, HDMI port, mini-HDMI port, USB port), Wi-Fi card, touchscreen (e.g., CRT, LCD, LED, AMOLED, Super AMOLED), pointing device, trackpad, microphone, speaker, light (e.g., LED), or light/image projection device.

Exemplary systems and system architectures for use with embodiments of the invention are described in U.S. Pub. 2011/0209133, U.S. Pub. 2011/0175923, and U.S. Pub. 2007/0112800, each of which is incorporated by reference herein in its entirety.

The software may further be transmitted or received over network 2021 via the network interface device.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A computer-implemented method, the method comprising:
   receiving information on clinical trial assets from one or more data sources;
   matching a portion of the information on the clinical trial assets with at least one user query;
   filtering the clinical trial assets in N-dimensional space according to one or more user criteria to identify an N-dimensional cluster of clinical trial assets;
   representing the identified N-dimensional cluster of clinical trial assets as one or more display elements;
   identifying an outlying display element by determining a centroid of a cluster of the one or more display elements and a distance between the outlying display element and the centroid; and
   modifying a visual aspect associated with the outlying display element to indicate at least one dimension of the outlying display element in the n-dimensional space has been reduced, wherein modifying the visual aspect comprises reducing the distance between the outlying display element and the centroid.

2. The method of claim 1, further comprising:
   reducing the distance of the outlying display element and the centroid of the N-dimensional cluster comprises transforming coordinates of the outlying display element.

3. The method of claim 1, wherein the user's criteria's include at least one of cost, research activity, and patient population.

4. The method of claim 1, wherein the clinical trial assets include at least one of a site, location, and/or an investigator.

5. The method of claim 1, further comprising:
   normalizing the matched portion of the information on the clinical trial assets received from the one or more data sources.

6. The method of claim 1, further comprising:
   merging the matched information of the clinical trial assets within a volatile memory after receiving the information on the clinical trial assets.

7. The method of claim 1, wherein N is an integer greater than or equal to 3.

8. A computer program product comprising a tangible storage medium encoded with processor-readable instructions that, when executed by one or more processors, enable the computer program product to:
   receive information on clinical trial assets from one or more data sources;
   match a portion of the information on the clinical trial assets with at least one user query;
   filter the clinical trial assets in N-dimensional space according to one or more user criteria to identify an N-dimensional cluster of clinical trial assets;
   represent each of the identified N-dimensional cluster of clinical trial assets as one or more display elements;
   identify an outlying display element by determining a centroid of a cluster of the one or more display elements and a distance between the outlying display element and the centroid; and
   modify a visual aspect associated with the outlying display element to indicate at least one dimension of the outlying display element in the n-dimensional space has been reduced, wherein modify the visual aspect comprises reducing the distance between the outlying display element and the centroid.

9. The computer program product of claim 8, wherein the user criteria's include at least one of research infrastructure and/or research activity.

10. The computer program product of claim 8, wherein one or more sets of research centers are within the N-dimensional cluster.

11. The computer program product of claim 8, wherein the centroid is located in a middle portion of the N-dimensional cluster.

12. The computer program product of claim 8, wherein the filter criteria includes local cost per patient and/or local availability of a specific comparator drug.

13. The computer program product of claim 8, wherein the outlying display element is represented by a nation/country.

14. The computer program product of claim 8, wherein the filtering includes determining whether the clinical trial assets supply a specific resource.

15. A computer system connected to a network, the system comprising:
    one or more processors configured to:
      receive information on clinical trial assets from one or more data sources;
      match a portion of the information on the clinical trial assets with at least one user query;
      filter the clinical trial assets in N-dimensional space according to one or more user criteria to identify an N-dimensional cluster of clinical trial assets;
      represent each of the identified N-dimensional cluster of clinical trial assets as one or more display elements;
      identify an outlying display element by determining a centroid of a cluster of the one or more display elements and a distance between the outlying display element and the centroid; and
      modify a visual aspect associated with the outlying display element to indicate at least one dimension of the outlying display element in the n-dimensional space has been reduced, wherein modify the visual aspect comprises reducing the distance between the outlying display element and the centroid.

16. The system of claim 15, wherein the filtering of the organized clinical trial assets is based on an availability of a diagnostic tool.

17. The system of claim 15, wherein the N-dimensional cluster of clinical trial assets are located within one or more cities.

18. The system of claim 15, wherein the filtering of the clinical trial assets includes filtering for one or more locations based on one or more questions being addressed.

19. The system of claim 15, wherein the information about the clinical trial assets are organized according to one or more diseases.

20. The system of claim 15, wherein each of the one or more display elements represent countries with one or more research facilities.

* * * * *